(12) United States Patent
Hale et al.

(10) Patent No.: US 6,649,640 B2
(45) Date of Patent: Nov. 18, 2003

(54) ISOXAZOLE COMPOSITIONS USEFUL AS INHIBITORS OF ERK

(75) Inventors: Michael Hale, Bedford, MA (US); James Janetka, Beverly, MA (US); Francois Maltais, Somerville, MA (US); Jingrong Cao, West Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/272,622

(22) Filed: Oct. 15, 2002

(65) Prior Publication Data

US 2003/0195241 A1 Oct. 16, 2003

Related U.S. Application Data

(62) Division of application No. 09/953,120, filed on Sep. 14, 2001, now Pat. No. 6,495,582.
(60) Provisional application No. 60/232,956, filed on Sep. 15, 2000.

(51) Int. Cl.$^7$ .................. A61K 31/422; C07D 413/04

(52) U.S. Cl. ...................... 514/378; 548/247

(58) Field of Search ............ 548/247; 514/378

(56) References Cited

U.S. PATENT DOCUMENTS

| 5,470,862 A | 11/1995 | Lin et al. ............ 514/341 |
| 5,498,720 A | 3/1996 | Lee ..................... 546/276 |

FOREIGN PATENT DOCUMENTS

| DE | 44 38 824 | 4/1995 |
| JP | 0827130 | 1/1996 |
| JP | 2000 086657 | 3/2000 |
| WO | WO 98/15542 | 4/1998 |
| WO | WO 98/35944 | 8/1998 |
| WO | WO 99/61440 | 12/1999 |
| WO | WO 01/56557 | 8/2001 |
| WO | WO 01/57022 | 8/2001 |

OTHER PUBLICATIONS

Holland et al, "Heterocyclic tetrazoles, a new class of lipolysis inhibitors", J. Med. Chem., 10(2): 149–154, 1967.

Almerico et al, "Polycondensed nitrogen heterocycles. Part 17. Isoxazolo–4,3–pyrazolo–3,4–f–1,2,3–triazepine. A new ring system", J. Heterocyclic Chem., 24(5): 1309–1311, 1987.

Tanaka et al, "Synthesis and properties of H–1,2,3–triazoles", Tetrahedron, 29(21): 3271–3285, 1973.

Bang et al, "Heteroaryl analogues of AMPA. Synthesis and quanitative structure–activity relationships", J. Med. Chem., 40(18): 2831–2842, 1997.

Jones et al, "1,3–Dipolar addition reactions with vinylpyrroles", Heterocycles, 14(2): 185–188, 1980.

Ajello et al, "New syntheses of condensed heterocycles from isoxazole derivatives. III. s–Triazolo[3,4]pyridazines", J. Het. Chem., 9(4): 1169–1170, 1972.

Aiello et al, "Synthesis and antimicrobial activity of new 3–(1R–3(5)–methyl–4–nitroso–1H–5(3)–pyrazolyl)–5–methylisoxazoles", Bioorg. Med. Chem., 8(12): 2719–2728, 2000.

Musante et al, *Gazz. Chim. Ital.,* 79, 1949.

*Primary Examiner*—Joseph K. McKane
*Assistant Examiner*—Rebecca Anderson
(74) *Attorney, Agent, or Firm*—Andrea L. C. Robidoux; Vertex Pharmaceuticals Incorporated

(57) ABSTRACT

Described herein are compounds that are useful as protein kinase inhibitors, especially inhibitors of ERK, having the formula:

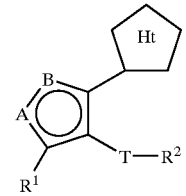

I where A, B, $R^1$, $R^2$, T and Ht are described in the specification. The compounds are useful for treating diseases in mammals that are alleviated by a protein kinase inhibitor, particularly diseases such as cancer, inflammatory disorders, restenosis, and cardiovascular disease.

10 Claims, No Drawings

ISOXAZOLE COMPOSITIONS USEFUL AS INHIBITORS OF ERK

CROSS-REFERENCE TO RELATED APPLICATIONS

This application is a divisional of co-pending U.S. patent application Ser. No. 09/953,120, filed Sep. 14, 2001 now U.S. Pat. No. 6,495,582, which claims priority to U.S. Provisional Patent Application 60/232,956 filed Sep. 15, 2000, the contents of which are incorporated herein by reference.

FIELD OF THE INVENTION

The present invention is in the field of medicinal chemistry and relates to isoxazole compounds that are protein kinase inhibitors, especially inhibitors of ERK, compositions containing such compounds and methods of use. The compounds are useful for treating cancer and other diseases that are alleviated by protein kinase inhibitors.

BACKGROUND OF THE INVENTION

Mammalian mitogen-activated protein (MAP)1 kinases are serine/threonine kinases that mediate intracellular signal transduction pathways (Cobb and Goldsmith, 1995, *J Biol. Chem.* 270, 14843; Davis, 1995, *Mol. Reprod. Dev.* 42, 459). Members of the MAP kinase family share sequence similarity and conserved structural domains, and include the ERK (extracellular signal regulated kinase), JNK (Jun N-terminal kinase) and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., 1994, *Cell* 76, 1025; Han et al., 1994, *Science* 265, 808; Raingeaud et al., 1995, *J Biol. Chem.* 270, 7420; Shapiro and Dinarello, 1995, *Proc. Natl. Acad. Sci. USA* 92, 12230). In contrast, ERKs are activated by mitogens and growth factors (Bokemeyer et al. 1996, *Kidney Int.* 49, 1187).

ERK2 is a widely distributed protein kinase that achieves maximum activity when both Thr183 and Tyr185 are phosphorylated by the upstream MAP kinase kinase, MEK1 (Anderson et al., 1990, *Nature* 343, 651; Crews et al., 1992, *Science* 258, 478). Upon activation, ERK2 phosphorylates many regulatory proteins, including the protein kinases Rsk90(Bjorbaek et al., 1995, *J. Biol. Chem.* 270, 18848) and MAPKAP2 (Rouse et al., 1994, *Cell* 78, 1027), and transcription factors such as ATF2 (Raingeaud et al., 1996, *Mol. Cell Biol.* 16, 1247), Elk-1 (Raingeaud et al. 1996), c-Fos (Chen et al., 1993 *Proc. Natl. Acad. Sci. USA* 90, 10952), and c-Myc (Oliver et al., 1995, *Proc. Soc. Exp. Biol. Med.* 210, 162). ERK2 is also a downstream target of the Ras/Raf dependent pathways (Moodie et al., 1993, *Science* 260, 1658) and may help relay the signals from these potentially oncogenic proteins. ERK2 has been shown to play a role in the negative growth control of breast cancer cells (Frey and Mulder, 1997, *Cancer Res.* 57, 628) and hyperexpression of ERK2 in human breast cancer has been reported (Sivaraman et al., 1997, *J Clin. Invest.* 99, 1478). Activated ERK2 has also been implicated in the proliferation of endothelin-stimulated airway smooth muscle cells, suggesting a role for this kinase in asthma (Whelchel et al., 1997, *Am. J. Respir. Cell Mol. Biol.* 16, 589).

AKT, also known as protein kinase B, is a serine/threonine kinase that plays a central role in promoting the survival of a wide range of cell types [Khwaja, A., *Nature*, pp. 33–34 (1990)]. It has been shown by Zang, et al, that human ovarian cancer cells display elevated levels of AKT-1 and AKT-2. Inhibition of AKT induces apoptosis of these human ovarian cancer cells which demonstrates that AKT may be an important target for ovarian cancer treatment [Zang, Q. Y., et al, *Oncogene*, 19 (2000)] and other proliferative disorders. The AKT pathway has also been implicated in motoneuronal survival and nerve regeneration [Kazuhiko, N., et al, *The Journal of Neuroscience*, 20 (2000)].

U.S. Pat. No. 5,470,862 discloses an isoxazole compound as an intermediate in the preparation of intravenous anesthetics.

There is a high unmet medical need to develop protein kinase inhibitors, especially ERK and AKT inhibitors especially considering the currently available, relatively inadequate treatment options for the majority of these conditions.

Accordingly, there is still a great need to develop potent inhibitors of protein kinase, including ERK and AKT inhibitors, that are useful in treating various conditions associated with protein kinase activation.

DESCRIPTION OF THE INVENTION

It has now been found that compounds of this invention and pharmaceutical compositions thereof are effective as protein kinase inhibitors, especially as inhibitors of ERK and AKT. These compounds have the general formula I:

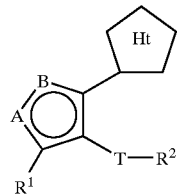

or a pharmaceutically acceptable derivative or prodrug thereof, wherein:

Ht is a heteroaryl ring selected from pyrrol-3-yl, pyrazol-3-yl, [1,2,4]triazol-3-yl, [1,2,3]triazol-4-yl, or tetrazol-5-yl; said pyrrol-3-yl and pyrazol-3-yl each having $R^3$ and $QR^4$ substituents, and said triazole substituted by either $R^3$ or $QR^4$;

A—B is N—O or O—N;

$R^1$ is selected from $R^5$, fluorine, $N(R^5)_2$, OR, NRCOR, $CON(R^5)_2$, $SO_2R$, $NRSO_2R$, or $SO_2N(R^5)_2$;

T and Q are each independently selected from a valence bond or a linker group;

each R is independently selected from hydrogen or an optionally substituted aliphatic group having one to six carbons;

$R^2$ is selected from hydrogen, CN, fluorine, or an optionally substituted group selected from aryl, heteroaryl, heterocyclyl, an acyclic aliphatic group having one to six carbons, or a cyclic aliphatic group having four to ten carbons; wherein $R^2$ has up to one L-W substituent and up to three $R^8$ substituents;

L is a $C_{1-6}$ alkylidene chain which is optionally substituted, and wherein up to two methylene units of L are optionally replaced by —C(O)—, —C(O)C(O)—, —CONH—, —CONHNH—, —CO$_2$—, —OC (O)—, —NHCO$_2$—, —O—, —NHCONH—, —OC(O)NH—, —NHNH—, —NHCO—, —S—, —SO—, —SO$_2$—, —NH—, —SO$_2$NH—, —NHSO$_2$NH—, or —NHSO$_2$—;

W is selected from R$^9$, CH(R$^9$)$_2$, CH(R$^9$)N(R$^9$)$_2$, or N(R$^9$)$_2$;

R$^3$ is selected from R, OH, OR, N(R)$_2$, fluorine, or CN;

R$^4$ is selected from —R$^6$, —NH$_2$, —NHR$^6$, —N(R$^6$)$_2$, or —NR$^6$ (CH$_2$)$_y$N(R$^6$)$_2$;

each R$^5$ is independently selected from hydrogen or an optionally substituted aliphatic group having one to six carbons or two R$^5$ on the same nitrogen may be taken together with the nitrogen to form a four to eight membered ring having one to three heteroatoms;

each R$^6$ is independently selected from R$^5$, —(CH$_2$)$_y$CH(R$^7$)$_2$, or —(CH$_2$)$_y$R$^7$;

y is 0–6;

each R$^7$ is an optionally substituted group independently selected from R, aryl, aralkyl, aralkoxy, heteroaryl, heteroarylalkyl, heteroarylalkoxy, heterocyclyl, heterocyclylalkyl, heterocyclylalkoxy, hydroxyalkyl, alkoxyalkyl, aryloxyalkyl, or alkoxycarbonyl;

each R$^8$ is independently selected from halogen, —R', —OR', —SR', —NO$_2$, —CN, —N(R$^5$)$_2$, —NRC(O)R', —NRC(O)N(R$^5$)$_2$, —NRCO$_2$R', —NRNRC(O)R', —NRNRC(O)N(R$^5$)$_2$, —NRNRCO$_2$R', —C(O)C(O)R', —C(O)CH$_2$C(O)R', —CO$_2$R', —C(O)R', —C(O)N(R$^5$)$_2$, —OC(O)N(R$^5$)$_2$, —S(O)$_2$R', —SO$_2$N(R$^5$)$_2$, —S(O)R', —NRSO$_2$N(R$^5$)$_2$, —NRSO$_2$R', —C(=S)N(R$^5$)$_2$, or —C(=NH)N(R$^5$)$_2$;

wherein each R' is independently selected from hydrogen, or an optionally substituted group selected from aliphatic, heteroaryl, heterocyclyl, or phenyl; and each R$^9$ is independently selected from R$^5$, R$^8$, or an optionally substituted group selected from aryl, aralkyl, aralkoxy, heteroaryl, heteroaralkyl, heterocyclyl, or heterocyclylalkyl.

As used herein, the following definitions shall apply unless otherwise indicated. In addition, unless otherwise indicated, functional group radicals are independently selected.

The term "aliphatic" as used herein means straight-chain, branched or cyclic C$_1$–C$_{12}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl) alkyl or (cycloalkyl)alkenyl. The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms. The term "cycloalkyl" used alone or as part of a larger moiety shall include cyclic C$_3$–C$_{12}$ hydrocarbons which are completely saturated or which contain one or more units of unsaturation, but which are not aromatic.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means N, O, or S and includes any oxidized form of nitrogen and sulfur, and the quaternized form of any basic nitrogen. It also includes =N— and —NR$^+$—, wherein R$^+$ is as defined infra.

The term "carbocycle", "carbocyclyl", or "carbocyclic" as used herein means an aliphatic ring system having three to fourteen members. The term "carbocycle", "carbocyclyl", or "carbocyclic" whether saturated or partially unsaturated, also refers to rings that are optionally substituted. The terms "carbocyclyl" or "carbocyclic" also include aliphatic rings that are fused to one or more aromatic or nonaromatic rings, such as in a decahydronaphthyl or tetrahydronaphthyl, where the radical or point of attachment is on the aliphatic ring.

The term "aryl" used alone or as part of a larger moiety as in "aralkyl", "aralkoxy", or "aryloxyalkyl", refers to aromatic ring groups having five to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having five to fourteen members, preferably five to ten, in which one or more ring carbons, preferably one to four, are each replaced by a heteroatom such as N, O, or S. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally-substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinoline, tetrahydroisoquinoline, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Examples of suitable substituents on the unsaturated carbon atom of an aryl, heteroaryl, aralkyl, or heteroaralkyl group include a halogen, —R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH) —N(R°)$_2$, —(CH$_2$)$_y$NHC(O)R°, —(CH$_2$)$_y$NHC(O)CH(V—R°) (R°); wherein R° is H, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph); y is 0–6; and V is a linker group. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An aliphatic group or a non-aromatic heterocyclic ring may contain one or more substituents. Examples of suitable substituents on the saturated carbon of an aliphatic group or of a non-aromatic heterocyclic ring include those listed above for the unsaturated carbon of an aryl or heteroaryl group and the following: =O, =s, =NNHR*, =NN(R*)$_2$, =N—, =NNHC(O)R*, =NNHCO$_2$(alkyl), =NNHSO$_2$(alkyl), or =NR*, where each R* is independently selected from hydrogen, an unsubstituted aliphatic group or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Suitable substituents on the nitrogen of an aromatic or non-aromatic heterocyclic ring include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH) —N(R$^+$)$_2$, and —NR$^+$SO$_2$R$^+$; wherein R$^+$ is H, an aliphatic group, a substituted aliphatic group, phenyl (Ph), substituted Ph, —O(Ph), substituted —O(Ph), CH$_2$(Ph), substituted CH$_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

The term "linker group" or "linker" means an organic moiety that connects two parts of a compound. Linkers are typically comprised of an atom such as oxygen or sulfur, a unit such as —NH—, —CH$_2$—, —C(O)—, —C(O)NH—, or a chain of atoms, such as an alkylidene chain. The molecular mass of a linker is typically in the range of about 14 to 200. Examples of linkers include a saturated or unsaturated C$_{1-6}$ alkylidene chain which is optionally substituted, and wherein one or two saturated carbons of the chain are optionally replaced by —C(O)—, —C(O)C(O)—, —CONH—, —CONHNH—, —CO$_2$—, —OC(O)—, —NHCO$_2$—, —O—, —NHCONH—, —OC(O)NH—, —NHNH—, —NHCO—, —S—, —SO—, —SO$_2$—, —NH—, —SO$_2$NH—, or —NHSO$_2$—.

The term "alkylidene chain" refers to an optionally substituted, straight or branched carbon chain that may be fully saturated or have one or more units of unsaturation. The optional substituents are as described above for an aliphatic group.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

One embodiment of this invention relates to compounds wherein A—B is N—O, shown by formula II:

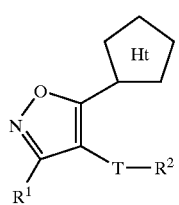

II or a pharmaceutically acceptable derivative or prodrug thereof, wherein R$^1$, R$^2$, R$^3$, R$^4$, T, and Q are as described above. Preferred embodiments of formula II are shown below for the Ht ring being pyrrol-3-yl (II-A), pyrazol-3-yl (II-B), [1,2,4]triazol-3-yl (II-C), [1,2,3]triazol-4-yl (II-D), and tetrazol-5-yl (II-E).

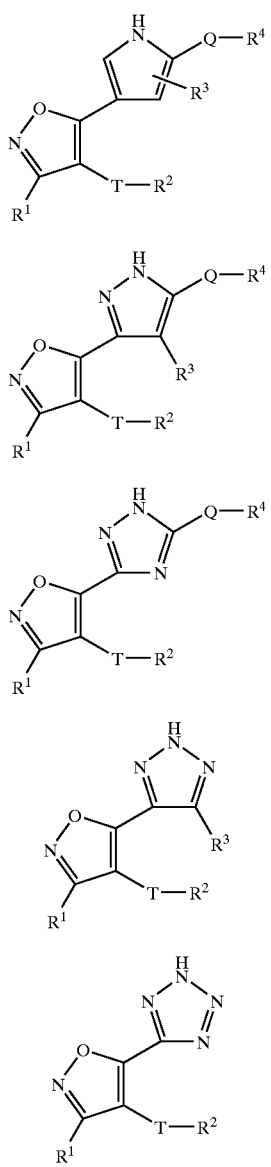

II-A

II-B

II-C

II-D

II-E

Preferred compounds of formulae II-A, II-B, II-C, II-D, and II-E include those having one or more, and most preferably all, of the following features: (a) Q is —CO—, —$CO_2$—, or —CONH—; (b) T is a valence bond, —NHC(O)—, or —$NHCH_2$—; (c) $R^1$ is hydrogen or NHR; (d) $R^2$ is an optionally substituted aryl ring, preferably a phenyl ring, and more preferably a phenyl ring having up to one L-W substituent and up to three $R^8$ substituents; (e) W is selected from $R^9$, $CH(R^9)_2$, $CH(R^9)N(R^9)_2$, or $N(R^9)_2$; (f) $R^3$ is hydrogen; (g) $R^4$ is selected from —$R^6$, —$NH_2$, —$NHR^6$, —$N(R^6)_2$, or —$NR^6(CH_2)_yN(R^6)_2$; (h) $R^6$ is $R^5$, —$(CH_2)_yCH(R^7)_2$, or —$(CH_2)_yR^7$; and/or (i) $R^7$ is an optionally substituted group selected from aryl, aralkyl, heteroaryl, heteroarylalkyl, heterocyclyl, or heterocyclylalkyl.

Preferred $R^8$ substituents on the $R^2$ phenyl group include halo, nitro, haloalkyl, hydroxyalkyl, $C_{1-6}$ aliphatic, alkoxy, amino, and heterocyclyl. Examples of preferred L groups include —$CH_2$—, —$CH_2NH$—, —$CH_2NHC(O)$—, —NH—, —$CH_2CH_2NH$—, —$CH_2O$—, —$CH_2C(O)NH$—, —$CH_2NHCH_2CH_2NHC(O)$—, and —$CH_2NHC(O)CH_2CH_2NHC(O)$—. Preferred W groups include —CH($C_{1-6}$ aliphatic)NC(O)($C_{1-6}$ aliphatic), —CH($CH_2OH$)NC(O)($C_{1-6}$ aliphatic), —CH($CH_2SH$)NC(O) ($C_{1-6}$ aliphatic), —N($C_{1-6}$ aliphatic )$_2$, -heterocyclyl (e.g. pyrrolidinyl, morpholinyl, thiomorpholinyl, and piperidinyl), —CH($C_{1-6}$ aliphatic)$NH_2$, —CH($C_{1-6}$ aliphatic)NC(O)O($C_{1-6}$ aliphatic), -$CH_2CN$, and —$CH_2N(C_{1-6}$ aliphatic)$_2$.

When $R^4$ is $R^6$, preferred $R^6$ groups include pyrrolidin-1-yl, morpholin-4-yl, piperidin-1-yl, and piperazin-1-yl wherein each group is optionally substituted. When $R^4$ is —$NHR^6$ or —$N(R^6)_2$, preferred $R^6$ groups further include $(CH_2)_yR^7$ and —$(CH_2)_yCH(R^7)_2$. Examples of preferred $R^6$ and $R^7$ include pyridin-3-yl, pyridin-4-yl, imidazolyl, furan-2-yl, tetrahydrofuran-2-yl, cyclohexyl, phenyl, —$CH_2OH$, —$(CH_2)_2$ OH, and isopropyl, wherein each group is optionally substituted.

Exemplary structures of formula II-A, wherein $R^1$ and $R^3$ are each hydrogen, are set forth in Table 1 below.

TABLE 1

II-A

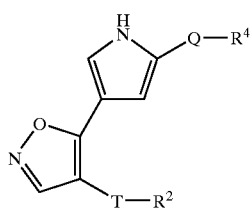

Compounds of Formula II-A

| No. | T—$R^2$ | Q—$R^4$ |
|---|---|---|
| IIA-1 | phenyl | CON(Me)$_2$ |
| IIA-2 | 2-chlorophenyl | CONHCH$_2$(Ph) |
| IIA-3 | 2-chlorophenyl | CO(morpholin-4-yl) |

TABLE 1-continued

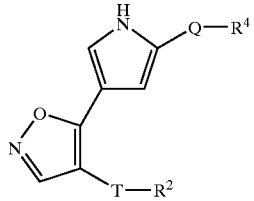

Compounds of Formula II-A

| No. | T—R² | Q—R⁴ |
|---|---|---|
| IIA-4 | 4-methoxyphenyl | CONHCH₂(pyridin-4-yl) |
| IIA-5 | 3-fluorophenyl | CONHCH₂(pyridin-4-yl) |
| IIA-6 | 3-methoxyphenyl | CONHCH₂(pyridin-4-yl) |
| IIA-7 | 2,5-dimethoxyphenyl | CONHCH₂(pyridin-4-yl) |
| IIA-8 | 3,4-difluorophenyl | CONHCH₂(pyridin-4-yl) |
| IIA-9 | 2,3-difluorophenyl | CONHCH₂(pyridin-4-yl) |
| IIA-10 | 2,5-difluorophenyl | CONHCH₂(pyridin-4-yl) |
| IIA-11 | 4-methoxyphenyl | CONHCH₂(pyridin-3-yl) |
| IIA-12 | 3-fluorophenyl | CONHCH₂(pyridin-3-yl) |
| IIA-13 | 3-methoxyphenyl | CONHCH₂(pyridin-3-yl) |
| IIA-14 | 2,5-dimethoxyphenyl | CONHCH₂(pyridin-3-yl) |
| IIA-15 | 3,4-difluorophenyl | CONHCH₂(pyridin-3-yl) |
| IIA-16 | 2,3-difluorophenyl | CONHCH₂(pyridin-3-yl) |
| IIA-17 | 2,5-difluorophenyl | CONHCH₂(pyridin-3-yl) |
| IIA-18 | 4-methoxyphenyl | CONHCH₂(tetrahydrofuran-2-yl) |
| IIA-19 | 3-fluorophenyl | CONHCH₂(tetrahydrofuran-2-yl) |
| IIA-20 | 3-methoxyphenyl | CONHCH₂(tetrahydrofuran-2-yl) |
| IIA-21 | 2,5-dimethoxyphenyl | CONHCH₂(tetrahydrofuran-2-yl) |
| IIA-22 | 3,4-difluorophenyl | CONHCH₂(tetrahydrofuran-2-yl) |
| IIA-23 | 2,3-difluorophenyl | CONHCH₂(tetrahydrofuran-2-yl) |
| IIA-24 | 2,5-difluorophenyl | CONHCH₂(tetrahydrofuran-2-yl) |
| IIA-25 | 4-fluorophenyl | CONHCH₂(1-Et-pyrrolidin-2-yl) |
| IIA-26 | 4-methoxyphenyl | CONHCH₂(1-Et-pyrrolidin-2-yl) |
| IIA-27 | 3-fluorophenyl | CONHCH₂(1-Et-pyrrolidin-2-yl) |
| IIA-28 | 3-methoxyphenyl | CONHCH₂(1-Et-pyrrolidin-2-yl) |
| IIA-29 | 2,5-dimethoxyphenyl | CONHCH₂(1-Et-pyrrolidin-2-yl) |
| IIA-30 | 3,4-difluorophenyl | CONHCH₂(1-Et-pyrrolidin-2-yl) |
| IIA-31 | 2,3-difluorophenyl | CONHCH₂(1-Et-pyrrolidin-2-yl) |
| IIA-32 | 2,5-difluorophenyl | CONHCH₂(1-Et-pyrrolidin-2-yl) |
| IIA-33 | 4-fluorophenyl | CO(morpholin-4-yl) |
| IIA-34 | 4-methoxyphenyl | CO(morpholin-4-yl) |
| IIA-35 | 3-fluorophenyl | CO(morpholin-4-yl) |
| IIA-36 | 3-methoxyphenyl | CO(morpholin-4-yl) |
| IIA-37 | 2,5-dimethoxyphenyl | CO(morpholin-4-yl) |
| IIA-38 | 2,3-difluorophenyl | CO(morpholin-4-yl) |
| IIA-39 | 2,5-difluorophenyl | CO(morpholin-4-yl) |
| IIA-40 | 4-fluorophenyl | CO(4-Me-piperazin-1-yl) |
| IIA-41 | 4-methoxyphenyl | CO(4-Me-piperazin-1-yl) |
| IIA-42 | 3-fluorophenyl | CO(4-Me-piperazin-1-yl) |
| IIA-43 | 3-methoxyphenyl | CO(4-Me-piperazin-1-yl) |
| IIA-44 | 2,5-dimethoxyphenyl | CO(4-Me-piperazin-1-yl) |
| IIA-45 | 2,3-difluorophenyl | CO(4-Me-piperazin-1-yl) |
| IIA-46 | 2,5-difluorophenyl | CO(4-Me-piperazin-1-yl) |
| IIA-47 | 3-chlorophenyl | CONHCH₂(pyridin-4-yl) |
| IIA-48 | 3-chlorophenyl | CONHCH₂(pyridin-3-yl) |
| IIA-49 | 3-chlorophenyl | CONHCH₂(tetrahydrofuran-2-yl) |
| IIA-50 | 3-chlorophenyl | CONHCH₂(1-Et-pyrrolidin-2-yl) |
| IIA-51 | 3-chlorophenyl | CO(4-Me-piperazin-1-yl) |
| IIA-52 | 4-chlorophenyl | CONHCH₂(pyridin-4-yl) |
| IIA-53 | 4-chloropheoyl | CONHCH₂(pyridin-3-yl) |
| IIA-54 | 4-chlorophenyl | CONHCH₂(tetrahydrofuran-2-yl) |
| IIA-55 | 4-chlorophenyl | CONHCH₂(1-Et-pyrrolidin-2-yl) |
| IIA-56 | 4-chlorophenyl | CO(morpholin-4-yl) |
| IIA-57 | 4-chlorophenyl | CO(4-Me-piperazin-1-yl) |
| IIA-58 | 3,4-dichlorophenyl | CONHCH₂(pyridin-3-yl) |
| IIA-59 | 3,4-dichlorophenyl | CONHCH₂(1-Et-pyrrolidin-2-yl) |
| IIA-60 | 3,4-dichlorophenyl | CO(morpholin-4-yl) |
| IIA-61 | 3,4-dichlorophenyl | CO(4-Me-piperazin-1-yl) |
| IIA-62 | 2-F-3-chlorophenyl | CONHCH₂(pyridin-4-yl) |
| IIA-63 | 2-F-3-chlorophenyl | CONHCH₂(pyridin-3-yl) |
| IIA-64 | 2-F-3-chlorophenyl | CONHCH₂(tetrahydrofuran-2-yl) |
| IIA-65 | 2-F-3-chlorophenyl | CONHCH₂(1-Et-pyrrolidin-2-yl) |
| IIA-66 | 2-F-3-chlorophenyl | CO(morpholin-4-yl) |

TABLE 1-continued

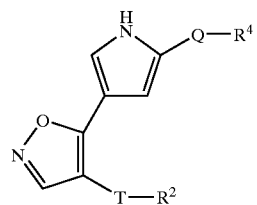

Compounds of Formula II-A

| No. | T—R² | Q—R⁴ |
|---|---|---|
| IIA-67 | 2-F-3-chlorophenyl | CO(4-Me-piperazin-1-yl) |
| IIA-68 | 3-Cl-4-fluorophenyl | CONHCH₂(pyridin-4-yl) |
| IIA-69 | 3-Cl-4-fluorophenyl | CONHCH₂(pyridin-3-yl) |
| IIA-70 | 3-Cl-4-fluorophenyl | CONHCH₂(tetrahydrofuran-2-yl) |
| IIA-71 | 3-Cl-4-fluorophenyl | CONHCH₂(1-Et-pyrrolidin-2-yl) |
| IIA-72 | 3-Cl-4-fluorophenyl | CO(morpholin-4-yl) |
| IIA-73 | 3-Cl-4-fluorophenyl | CO(4-Me-piperazin-1-yl) |
| IIA-74 | 3,4-dimethoxyphenyl | CONHCH₂(pyridin-4-yl) |
| IIA-75 | 3,4-dimethoxyphenyl | CONHCH₂(pyridin-3-yl) |
| IIA-76 | 3,4-dimethoxyphenyl | CONHCH₂(tetrahydrofuran-2-yl) |
| IIA-77 | 3,4-dimethoxyphenyl | CONHCH₂(1-Et-pyrrolidin-2-yl) |
| IIA-78 | 3,4-dimethoxyphenyl | CO(morpholin-4-yl) |
| IIA-79 | 3,4-dimethoxyphenyl | CO(4-Me-piperazin-1-yl) |
| IIA-80 | 4-benzo[1,3]dioxol-5-yl | CONHCH₂(pyridin-4-yl) |
| IIA-81 | 4-benzo[1,3]dioxol-5-yl | CONHCH₂(pyridin-3-yl) |
| IIA-82 | 4-benzo[1,3]dioxol-5-yl | CONHCH₂(tetrahydrofuran-2-yl) |
| IIA-83 | 4-benzo[1,3]dioxol-5-yl | CONHCH₂(1-Et-pyrrolidin-2-yl) |
| IIA-84 | 4-benzo[1,3]dioxol-5-yl | CO(morpholin-4-yl) |
| IIA-85 | 4-benzo[1,3]dioxol-5-yl | CO(4-Me-piperazin-1-yl) |
| IIA-86 | 3,5-dichlorophenyl | CONHCH₂(pyridin-4-yl) |
| IIA-87 | 3,5-dichlorophenyl | CONHCH₂(pyridin-3-yl) |
| IIA-88 | 3,5-dichlorophenyl | CONHCH₂(tetrahydrofuran-2-yl) |
| IIA-89 | 3,5-dichlorophenyl | CONHCH₂(1-Et-pyrrolidin-2-yl) |
| IIA-90 | 3,5-dichlorophenyl | CO(morpholin-4-yl) |
| IIA-91 | 3,5-dichlorophenyl | CO(4-Me-piperazin-1-yl) |
| IIA-92 | 3-Cl-4-SO₂NH₂-phenyl | CO(morpholin-4-yl) |
| IIA-93 | 3-chlorophenyl | CO(morpholin-4-yl) |
| IIA-94 | phenyl | pyridin-4-yl |
| IIA-95 | 2-chlorophenyl | morpholin-4-yl |
| IIA-96 | 2-chlorophenyl | CH₂(morpholin-4-yl) |
| IIA-97 | 4-methoxyphenyl | CH₂(pyridin-4-yl) |

IIA-98

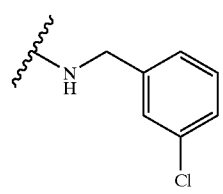 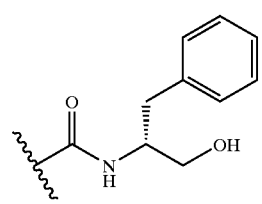

IIA-99

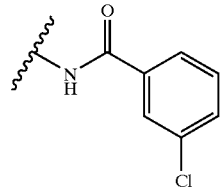 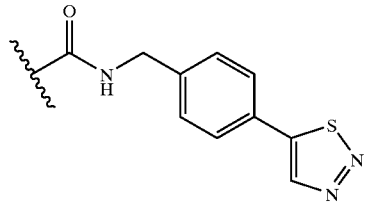

IIA-100

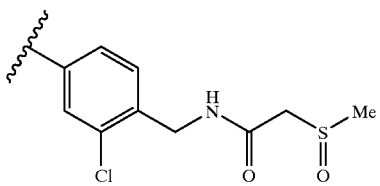 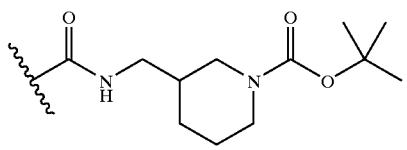

TABLE 1-continued

Compounds of Formula II-A (II-A)

| No. | T—R² | Q—R⁴ |
|---|---|---|
| IIA-101 | 4-(2-chlorobenzyl) with NHC(O)CH(NHAc)CH₃ substituent | piperazine-N-C(O)- linked to 3-methoxyphenyl |
| IIA-102 | 4-(2-chlorobenzyl) with NHC(O)CH₂N(CH₃)₂ | -C(O)NH-CH(CH₂OH)-(3,5-dichlorophenyl) |
| IIA-103 | 4-(2-chlorobenzyl) with NHC(O)CH(NHAc)CH₂SH | -C(O)NH-CH(CH₂Ph)-C(O)OCH₃ |
| IIA-104 | 4-(2-chlorobenzyl) with NHC(O)-(N-acetyl-prolinyl) | -C(O)NHCH₂-(1-Boc-piperidin-3-yl) |
| IIA-105 | -NHC(O)-(2-chloro-4-benzyl) with NHC(O)CH(NHAc)CH₂SH | -C(O)NHCH₂CH₂-(1H-imidazol-4-yl) |
| IIA-106 | phenyl | piperazine-N-C(O)- linked to 2-fluorophenyl |

TABLE 1-continued

Compounds of Formula II-A

| No. | T—R² | Q—R⁴ |
|---|---|---|
| IIA-107 | phenyl | piperazine-N-phenyl carbonyl |
| IIA-108 | 3,4-dimethoxyphenyl | piperazine-N-(2-fluorophenyl) carbonyl |
| IIA-109 | 3-chlorophenyl | piperazine-N-phenyl carbonyl |
| IIA-110 | 3-chlorophenyl | 1,2,3,4-tetrahydroisoquinoline-2-carbonyl |
| IIA-111 | 3-methylphenyl | 1,2,3,4-tetrahydroisoquinoline-2-carbonyl |
| IIA-112 | 3-chlorophenyl | N-methyl-N-benzyl carbamoyl |
| IIA-113 | 2-fluoro-3-chlorophenyl | N-methyl-N-benzyl carbamoyl |

TABLE 1-continued
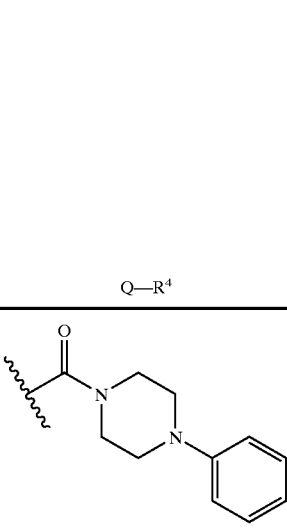
Compounds of Formula II-A
| No. | T—R² | Q—R⁴ |
|---|---|---|
| IIA-114 | 2-fluoro-3-chlorophenyl | 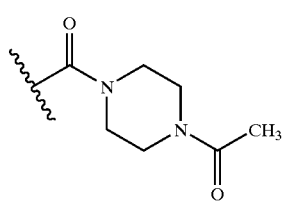 |
| IIA-115 | 3-chlorophenyl | 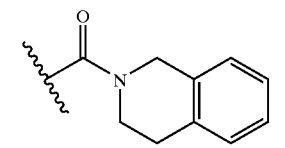 |
| IIA-116 | 3,4-dimethoxyphenyl | 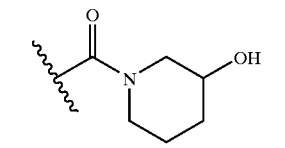 |
| IIA-117 | 3,4-dimethoxyphenyl | 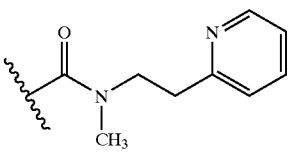 |
| IIA-118 | 3,4-dimethoxyphenyl | 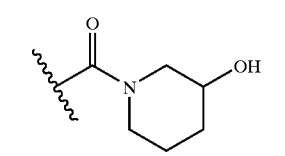 |
| IIA-119 | 3-methylphenyl | 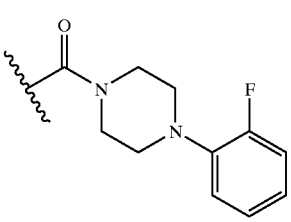 |
| IIA-120 | 2-fluoro-3-chlorophenyl | |

TABLE 1-continued

Compounds of Formula II-A

II-A

| No. | T—R² | Q—R⁴ |
| --- | --- | --- |
| IIA-121 | 2-fluoro-3-chlorophenyl | piperazine-C(O)- linked, N'-(4-methoxyphenyl) |
| IIA-122 | 2-fluoro-3-chlorophenyl | piperazine-C(O)- linked, N'-(2-hydroxyethyl) |
| IIA-123 | 3-chlorophenyl | 4-(piperidin-1-yl)piperidine-1-carbonyl |
| IIA-124 | 3,4-dimethoxyphenyl | 2-(2-hydroxyethyl)piperidine-1-carbonyl |
| IIA-125 | 2-fluoro-3-chlorophenyl | 2-(2-hydroxyethyl)piperidine-1-carbonyl |
| IIA-126 | 2-fluoro-3-chlorophenyl | piperazine-C(O)- linked, N'-(pyridin-2-yl) |

TABLE 1-continued
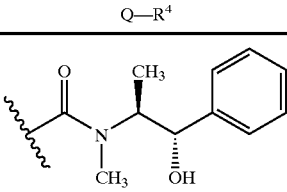
Compounds of Formula II-A
| No. | T—R² | Q—R⁴ |
|---|---|---|
| IIA-127 | 3,4-dimethoxyphenyl | 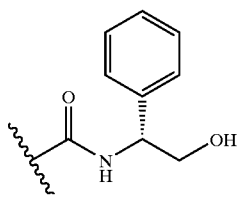 |
| IIA-128 | 3,5-dichlorophenyl | 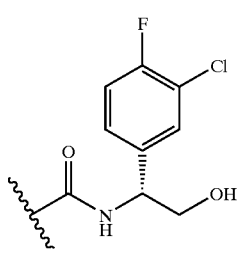 |
| IIA-129 | 3,5-dichlorophenyl | 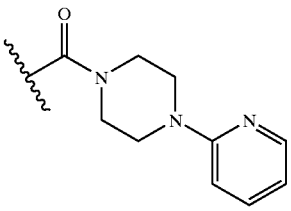 |
| IIA-130 | phenyl | 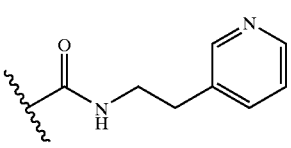 |
| IIA-131 | phenyl | 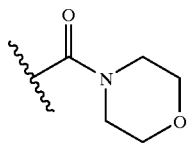 |
| IIA-132 | phenyl | 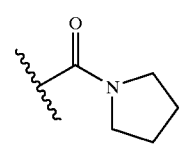 |
| IIA-133 | phenyl |  |

TABLE 1-continued
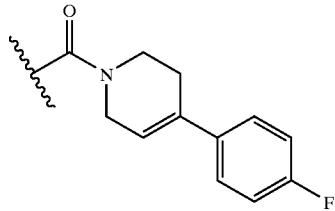
Compounds of Formula II-A
| No. | T—R² | Q—R⁴ |
|---|---|---|
| IIA-134 | phenyl | 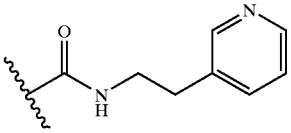 |
| IIA-135 | 3,4-dimethoxyphenyl | 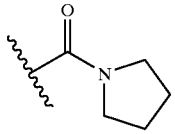 |
| IIA-136 | 3,4-dimethoxyphenyl | 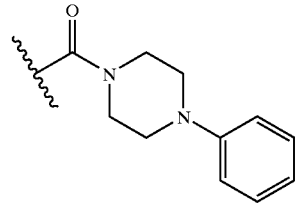 |
| IIA-137 | 3,4-dimethoxyphenyl | 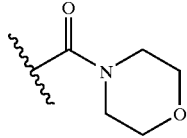 |
| IIA-138 | 3-methylphenyl | 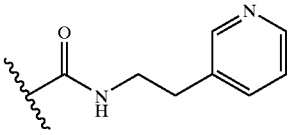 |
| IIA-139 | 3-methylphenyl | 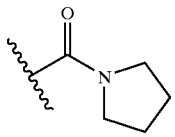 |
| IIA-140 | 3-methylphenyl | |

TABLE 1-continued
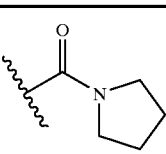
Compounds of Formula II-A
| No. | T—R² | Q—R⁴ |
|---|---|---|
| IIA-141 | 2-fluoro,3-chlorophenyl | 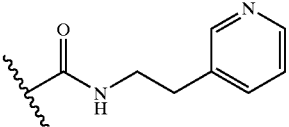 |
| IIA-142 | 3-chlorophenyl | 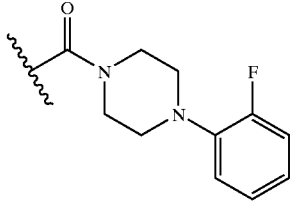 |
| IIA-143 | 3-chlorophenyl | 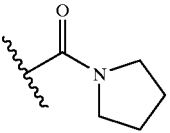 |
| IIA-144 | 3-chlorophenyl | 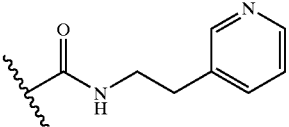 |
| IIA-145 | 3-chlorophenyl | 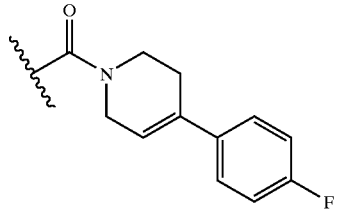 |
| IIA-146 | 3-chlorophenyl | 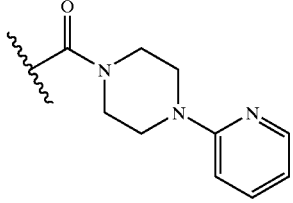 |
| IIA-147 | phenyl | 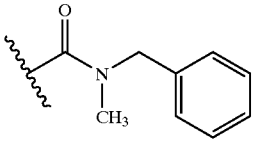 |

TABLE 1-continued

Compounds of Formula II-A

II-A

| No. | T—R² | Q—R⁴ |
|---|---|---|
| IIA-148 | phenyl | piperazine-C(O)- linked, N'-(4-methoxyphenyl) |
| IIA-149 | 3,4-dimethoxyphenyl | -C(O)-N(CH₃)(CH₂-phenyl) |
| IIA-150 | 3,4-dimethoxyphenyl | 4-(4-fluorophenyl)-1,2,3,6-tetrahydropyridine-1-carbonyl |
| IIA-151 | 3-methylphenyl | 4-phenylpiperazine-1-carbonyl |
| IIA-152 | 3-methylphenyl | 4-methyl-1,4-diazepane-1-carbonyl |
| IIA-153 | phenyl | 2-(hydroxymethyl)piperidine-1-carbonyl |

TABLE 1-continued

Compounds of Formula II-A

| No. | T—R² | Q—R⁴ |
|---|---|---|
| IIA-154 | phenyl | 4-methyl-1,4-diazepane-1-carbonyl |
| IIA-155 | phenyl | 3,4-dihydroisoquinoline-2(1H)-carbonyl |
| IIA-156 | 3,4-dimethoxyphenyl | 4-(4-methoxyphenyl)piperazine-1-carbonyl |
| IIA-157 | 3,4-dimethoxyphenyl | 4-acetylpiperazine-1-carbonyl |
| IIA-158 | 3-methylphenyl | N-benzyl-N-methylcarbamoyl |
| IIA-159 | 3-methylphenyl | 2-(hydroxymethyl)piperidine-1-carbonyl |
| IIA-160 | 3-chlorophenyl | 2-(hydroxymethyl)piperidine-1-carbonyl |

TABLE 1-continued

Compounds of Formula II-A

II-A

| No. | T—R² | Q—R⁴ |
|---|---|---|
| IIA-161 | phenyl | piperidine-N-carbonyl with 2-(2-hydroxyethyl) substituent |
| IIA-162 | 3-chlorophenyl | piperidine-N-carbonyl with 2-(2-hydroxyethyl) substituent |
| IIA-163 | 3,4-dimethoxyphenyl | 4-methyl-1,4-diazepane-1-carbonyl |
| IIA-164 | 3-chlorophenyl | 4-methyl-1,4-diazepane-1-carbonyl |
| IIA-165 | phenyl | 3-hydroxypiperidine-1-carbonyl |
| IIA-166 | phenyl | N,N-bis(2-hydroxyethyl)carbamoyl |

TABLE 1-continued

Compounds of Formula II-A

II-A

| No. | T—R² | Q—R⁴ |
|---|---|---|
| IIA-167 | phenyl | 4-acetylpiperazine-1-carbonyl |
| IIA-168 | 3,4-dimethoxyphenyl | 2-(hydroxymethyl)piperidine-1-carbonyl |
| IIA-169 | 3,4-5dimethoxyphenyl | 4-(piperidin-1-yl)piperidine-1-carbonyl |
| IIA-170 | 3,4-dimethoxyphenyl | 4-(2-fluorophenyl)piperazine-1-carbonyl |
| IIA-171 | 3-methylphenyl | 3-hydroxypiperidine-1-carbonyl |
| IIA-172 | 3-methylphenyl | 4-(4-methoxyphenyl)piperazine-1-carbonyl |

TABLE 1-continued
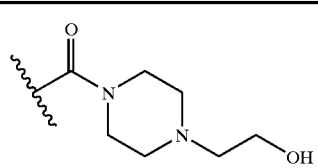
Compounds of Formula II-A
| No. | T—R² | Q—R⁴ |
|---|---|---|
| IIA-173 | 3-methylphenyl | 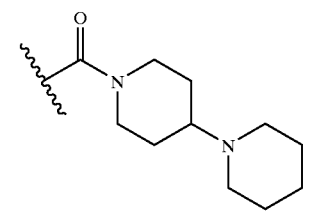 |
| IIA-174 | 3-methylphenyl | 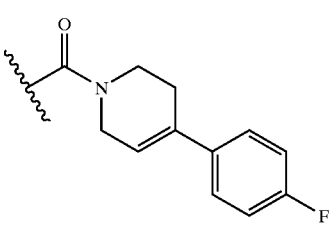 |
| IIA-175 | 3-methylphenyl | 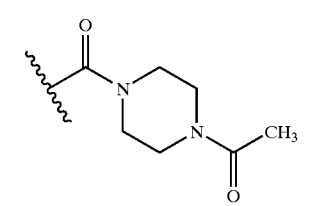 |
| IIA-176 | 3-methylphenyl | 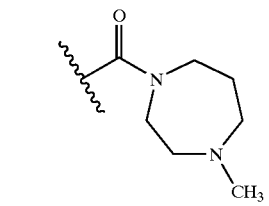 |
| IIA-177 | 2-fluoro,3-chlorophenyl | 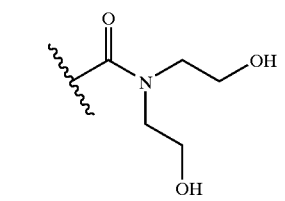 |
| IIA-178 | 2-fluoro,3-chlorophenyl | |

TABLE 1-continued

Compounds of Formula II-A

II-A

| No. | T—R² | Q—R⁴ |
|---|---|---|
| IIA-179 | 2-fluoro,3-chlorophenyl | 4-acetylpiperazine-1-carbonyl |
| IIA-180 | 2-fluoro,3-chlorophenyl | 3,4-dihydroisoquinoline-2(1H)-carbonyl |
| IIA-181 | phenyl | N-methyl-N-[(1S,2S)-2-hydroxy-1-methyl-2-phenylethyl]carbamoyl |
| IIA-182 | 3-chlorophenyl | 3-hydroxypiperidine-1-carbonyl |
| IIA-183 | 3-chlorophenyl | 4-(4-methoxyphenyl)piperazine-1-carbonyl |
| IIA-184 | 3-chlorophenyl | 4-(2-hydroxyethyl)piperazine-1-carbonyl |
| IIA-185 | 3-chlorophenyl | N,N-bis(2-hydroxyethyl)carbamoyl |

TABLE 1-continued
Compounds of Formula II-A
| No. | T—R² | Q—R⁴ |
|---|---|---|
| IIA-186 | 3-chlorophenyl | 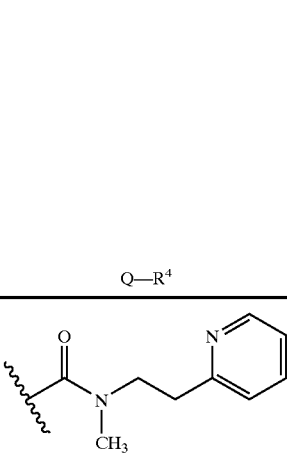 |
| IIA-187 | 3-methylphenyl | 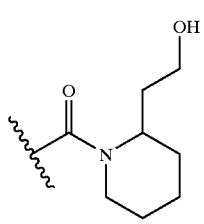 |
| IIA-188 | 3-methylphenyl | 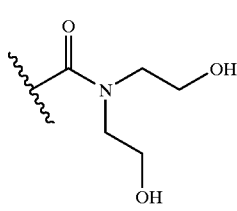 |
| IIA-189 | 2-fluoro,3-chlorophenyl | 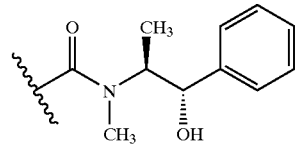 |
| IIA-190 | 2-fluoro,3-chlorophenyl | 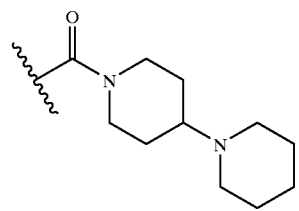 |
| IIA-191 | phenyl | 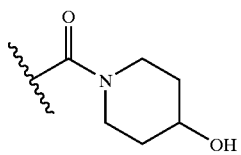 |
| IIA-192 | 3,4-dimethoxyphenyl | 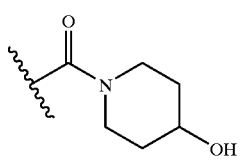 |

TABLE 1-continued

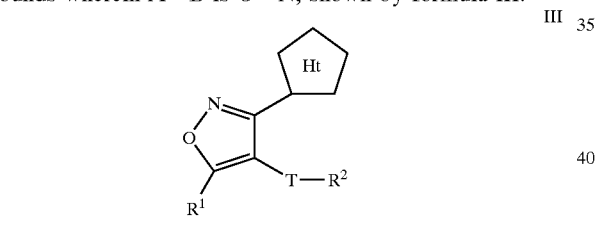

Compounds of Formula II-A

| No. | T—R² | Q—R⁴ |
|---|---|---|
| IIA-193 | 3-methylphenyl | 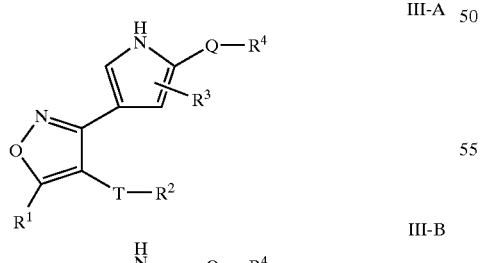 |
| IIA-194 | phenyl | 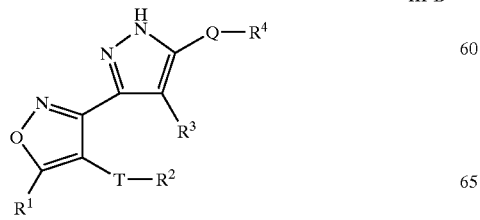 |

Another embodiment of this invention relates to compounds wherein A—B is O—N, shown by formula III:

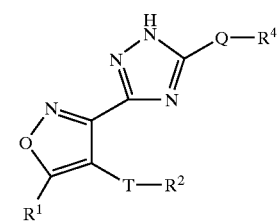

or a pharmaceutically acceptable derivative or prodrug thereof, wherein R¹, R², T, and Q are as described above. Preferred embodiments of formula III are shown below for the Ht ring being pyrrol-3-yl (III-A), pyrazol-3-yl (III-B), [1,2,4]triazol-3-yl (III-C), [1,2,3]triazol-4-yl (III-D), and tetrazol-5-yl (III-E).

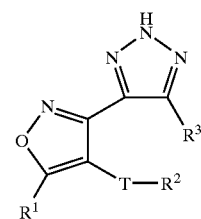

Preferred compounds of formulae III-A, III-B, III-C, III-D, and III-E include those having one or more, and most preferably all, of the following features: (a) Q is —CO—, —CO$_2$—, or —CONH—; (b) T is a valence bond, —NHC(O)—, or —NHCH$_2$—; (c) R$^1$ is hydrogen or NHR; (d) R$^2$ is an optionally substituted aryl ring, preferably a phenyl ring, and more preferably a phenyl ring having up to one L-W substituent and up to three R$^8$ substituents; (e) W is selected from R$^9$, CH(R$^9$)$_2$, CH(R$^9$)N(R$^9$)$_2$, or N(R$^9$)$_2$; (f) R$^3$ is hydrogen; (g) R$^4$ is selected from —R$^6$, —NH$_2$, —NHR$^6$, —N(R$^6$)$_2$, or —NR$^6$(CH$_2$)$_y$N(R$^6$)$_2$; (h) R$^6$ is R$^5$, —(CH$_2$)$_y$CH(R$^7$)$_2$, or —(CH$_2$)$_y$R$^7$; and/or (i) R$^7$ is an optionally substituted group selected from aryl, aralkyl, heteroaryl, heteroarylalkyl, heterocyclyl, or heterocyclylalkyl.

Preferred R$^8$ substituents of the R$^2$ phenyl group, if present, include halo, nitro, haloalkyl, hydroxyalkyl, C$_{1-6}$ aliphatic, alkoxy, amino, and heterocyclyl. Preferred L groups include —CH$_2$—, —CH$_2$NH—, —CH$_2$NHC(O)—, —NH—, —CH$_2$CH$_2$NH—, —CH$_2$O—, —CH$_2$C(O)NH—, —CH$_2$NHCH$_2$CH$_2$NHC(O)—, and —CH$_2$NHC(O)CH$_2$CH$_2$NHC(O)—. Preferred W groups include —CH(C$_{1-6}$ aliphatic)NC(O)(C$_{1-6}$ aliphatic), —CH(CH$_2$OH)NC(O)(C$_{1-6}$ aliphatic), —CH(CH$_2$SH) NC(O) (C$_{1-6}$ aliphatic), N(C$_{1-6}$ aliphatic)$_2$, heterocyclyl (e.g. pyrrolidinyl, morpholinyl, thiomorpholinyl, and piperidinyl), —CH(C$_{1-6}$ aliphatic)NH$_2$, —CH(C$_{1-6}$ aliphatic)NC(O)O(C$_{1-6}$ aliphatic), —CH$_2$CN, and —CH$_2$N(C$_{1-6}$ aliphatic)$_2$.

When R$^4$ is R$^6$, preferred R$^6$ groups include pyrrolidin-1-yl, morpholin-4-yl, piperidin-1-yl, and piperazin-1-yl wherein each group is optionally substituted. When R$^4$ is —NHR$^6$ or —N(R$^6$)$_2$, preferred R$^6$ groups further include (CH$_2$)$_x$R$^7$ and —(CH$_2$)$_y$CH(R$^7$)$_2$. Examples of preferred R$^6$ and R$^7$ include pyridin-3-yl, pyridin-4-yl, imidazolyl, furan-2-yl, tetrahydrofuran-2-yl, cyclohexyl, phenyl, —CH$_2$OH, —(CH$_2$)$_2$ OH, and isopropyl, wherein each group is optionally substituted.

Exemplary structures of formula III-A, wherein R$^1$ and R$^3$ are each hydrogen, are set forth in Table 2 below.

TABLE 2

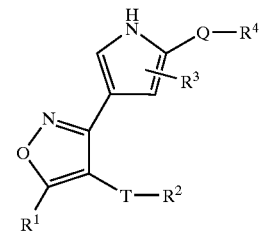

Compounds of Formula III-A

| No. | T—R$^2$ | Q—R$^4$ |
|---|---|---|
| IIIA-1 | phenyl | CON(Me)$_2$ |
| IIIA-2 | 2-chlorophenyl | CONHCH$_2$(Ph) |
| IIIA-3 | 2-chlorophenyl | CO(morpholin-4-yl) |
| IIIA-4 | 4-methoxyphenyl | CONHCH$_2$(pyridin-4-yl) |
| IIIA-5 | 3-fluorophenyl | CONHCH$_2$(pyridin-4-yl) |
| IIIA-6 | 3-methoxyphenyl | CONHCH$_2$(pyridin-4-yl) |
| IIIA-7 | 2,5-dimethoxyphenyl | CONHCH$_2$(pyridin-4-yl) |
| IIIA-8 | 3,4-difluorophenyl | CONHCH$_2$(pyridin-4-yl) |
| IIIA-9 | 2,3-difluorophenyl | CONHCH$_2$(pyridin-4-yl) |
| IIIA-10 | 2,5-difluorophenyl | CONHCH$_2$(pyridin-4-yl) |
| IIIA-11 | 4-methoxyphenyl | CONHCH$_2$(pyridin-3-yl) |
| IIIA-12 | 3-fluorophenyl | CONHCH$_2$(pyridin-3-yl) |
| IIIA-13 | 3-methoxyphenyl | CONHCH$_2$(pyridin-3-yl) |
| IIIA-14 | 2,5-dimethoxyphenyl | CONHCH$_2$(pyridin-3-yl) |
| IIIA-15 | 3,4-difluorophenyl | CONHCH$_2$(pyridin-3-yl) |
| IIIA-16 | 2,3-difluorophenyl | CONHCH$_2$(pyridin-3-yl) |
| IIIA-17 | 2,5-difluorophenyl | CONHCH$_2$(pyridin-3-yl) |
| IIIA-18 | 4-methoxyphenyl | CONHCH$_2$(tetrahydrofuran-2-yl) |

TABLE 2-continued

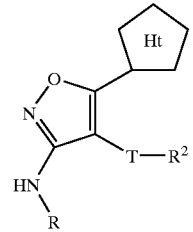

Compounds of Formula III-A

| No. | T—R$^2$ | Q—R$^4$ |
|---|---|---|
| IIIA-19 | 2,5-difluorophenyl | CONHCH$_2$(1-Et-pyrrolidin-2-yl) |
| IIIA-20 | 4-fluorophenyl | CO(morpholin-4-yl) |
| IIIA-21 | 4-fluorophenyl | CO(4-Me-piperazin-1-yl) |

According to another embodiment, the present invention relates to compounds of formula IV:

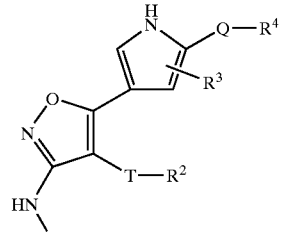

or a pharmaceutically acceptable derivative or prodrug thereof, wherein R$^1$, R$^2$, T, and Q are as described above. Preferred embodiments of formula IV are shown below for the Ht ring being pyrrol-3-yl (IV-A), pyrazol-3-yl (IV-B), [1,2,4]triazol-3-yl (IV-C), [1,2,3]triazol-4-yl (IV-D), and tetrazol-5-yl (IV-E).

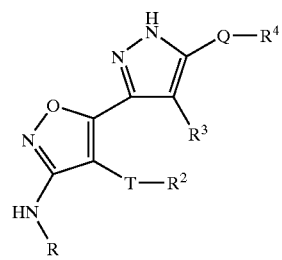

IV-C

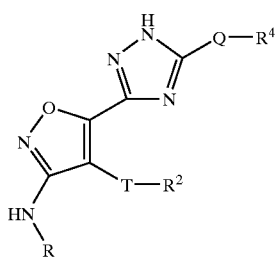

IV-D

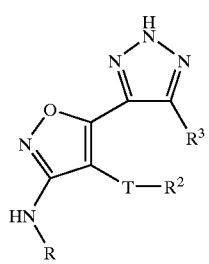

IV-E

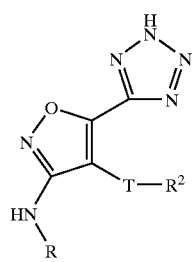

Preferred compounds of formulae IV-A, IV-B, IV-C, IV-D, and IV-E include those having one or more, and most preferably all, of the following features: (a) Q is —CO—, —CO₂—, or —CONH—; (b) T is a valence bond, —NHC(O)—, or —NHCH₂—; (c) $R^2$ is an optionally substituted aryl ring, more preferably a phenyl ring having up to one L-W substituent and up to three $R^8$ substituents; (d) $R^3$ is hydrogen; (e) $R^4$ is selected from —$R^6$, —NH₂, —NHR⁶, —N($R^6$)₂, or —NR⁶(CH₂)$_y$N(R )₂; (f) $R^6$ is $R^5$, —(CH₂)$_y$CH($R^7$)₂, or —(CH₂)$_y R^7$; and/or (g) $R^7$ is an optionally substituted group selected from aryl, aralkyl, heteroaryl, heteroarylalkyl, heterocyclyl, heterocyclylalkyl group.

Preferred $R^8$ substituents of the $R^2$ phenyl group, if present, include halo, nitro, haloalkyl, hydroxyalkyl, $C_{1-6}$ aliphatic, alkoxy, amino, and heterocyclyl.

When $R^4$ is $R^6$, preferred $R^6$ groups include pyrrolidin-1-yl, morpholin-4-yl, piperidin-1-yl, and piperazin-1-yl wherein each group is optionally substituted. When $R^4$ is —NHR⁶ or —N($R^6$)₂, preferred $R^6$ groups further include (CH₂)$_y R^7$ and —(CH₂)$_y$CH($R^7$)₂. Examples of preferred $R^6$ and $R^7$ include pyridin-3-yl, pyridin-4-yl, imidazolyl, furan-2-yl, tetrahydrofuran-2-yl, cyclohexyl, phenyl, —CH₂OH, —(CH₂)₂ OH, and isopropyl, wherein each group is optionally substituted.

Exemplary structures of formula IV-A, wherein $R^3$ is hydrogen, are set forth in Table 3 below.

TABLE 3

IV-A

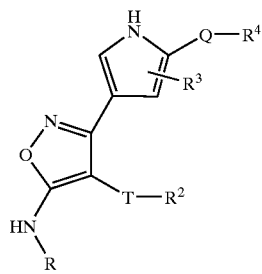

Compounds IV-A

| No. | R | T—R² | Q—R⁴ |
|---|---|---|---|
| IVA-1 | H | phenyl | CON(Me)₂ |
| IVA-2 | H | phenyl | CO₂Et |
| IVA-3 | H | 3-NO₂-phenyl | CONHNH₂ |
| IVA-4 | H | phenyl | CO(pyrrolidin-1-yl) |
| IVA-5 | Me | phenyl | CONHCH₂(Ph) |
| IVA-6 | H | 3-NO₂-phenyl | CO₂Et |
| IVA-7 | H | 4-Cl-phenyl | CO₂Et |
| IVA-8 | Me | 4-OMe-phenyl | CO₂Et |
| IVA-9 | H | 3-NH₂-phenyl | CO₂Et |
| IVA-10 | H | 3-OMe-phenyl | CO₂Et |
| IVA-11 | H | 4-F-phenyl | CO₂Et |
| IVA-12 | H | 4-NO₂-phenyl | CO₂Et |
| IVA-13 | Et | 3-Cl-phenyl | CO₂Et |
| IVA-14 | H | 3-F-phenyl | CO₂Et |
| IVA-15 | H | phenyl | CO₂H |

TABLE 3-continued

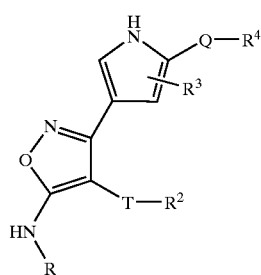

Compounds IV-A

| No. | R | T—R² | Q—R⁴ |
|---|---|---|---|
| IVA-16 | Me | 3-Cl-phenyl | CONHCH$_2$(pyridin-4-yl) |
| IVA-17 | H | 5-Cl-phenyl | ![structure: C(=O)NH-indanyl-OH] |
| IVA-18 | H | 5-F-phenyl | CONHCH$_2$(tetrahydrofuran-2-yl) |
| IVA-19 | Me | 5,6-F$_2$-phenyl | CO(4-Me-piperidin-1-yl) |
| IVA-20 | H | 4-Cl-phenyl | CONHCH$_2$(pyrid-4-yl) |
| IVA-21 | H | 4,5-(OMe)$_2$-phenyl | ![structure: C(=O)NHCH$_2$CH$_2$-imidazolyl] |
| IVA-22 | Me | 4,5-Cl$_2$-phenyl | ![structure: C(=O)NHCH$_2$-(N-Boc-piperidin-3-yl)] |
| IVA-23 | H | 3-Cl-phenyl | ![structure: C(=O)NH-CH(Ph)-CH$_2$-OC(=O)CH$_3$] |
| IVA-24 | H | 3-Cl-phenyl | ![structure: C(=O)NH-CH(3,5-diCl-phenyl)-CH$_2$OH] |
| IVA-25 | Me | 3,5-Cl$_2$-phenyl | ![structure: C(=O)NH-CH(3-Cl-4-F-phenyl)-CH$_2$OH] |

TABLE 3-continued

IV-A

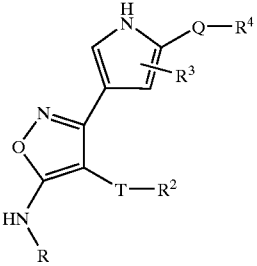

Compounds IV-A

| No. | R | T—R² | Q—R⁴ |
|---|---|---|---|
| IVA-26 | H | 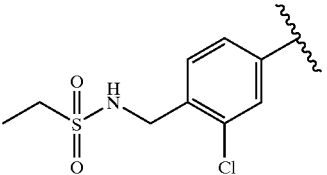 | 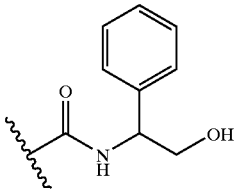 |
| IVA-27 | H | 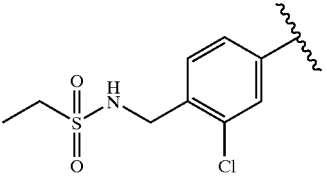 | CON(Me)₂ |

According to another embodiment, the present invention relates to compounds, wherein T is a valence bond and $R^2$ is a phenyl ring substituted with L-W and up to three $R^8$, of formula V:

V

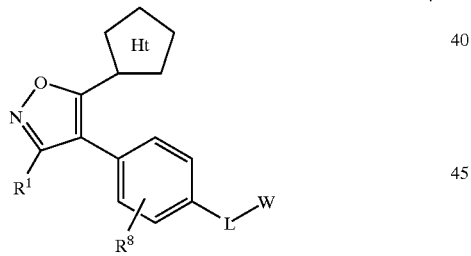

or a pharmaceutically acceptable derivative or prodrug thereof, wherein R, $R^1$, $R^3$, $R^4$, $R^8$, L, and W are as described above. Preferred embodiments are shown below for the Ht ring being pyrrol-3-yl.(V-A), pyrazol-3-yl (V-B), [1,2,4]triazol-3-yl (V-C), [1,2,3]triazol-4-yl (V-D), and tetrazol-5-yl (V-E).

V-A

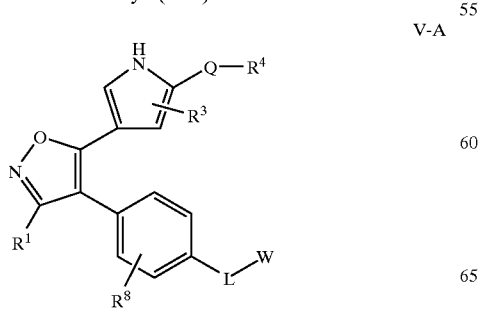

V-B

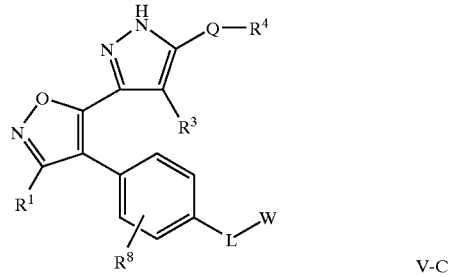

V-C

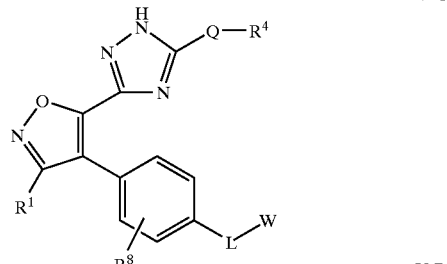

V-D

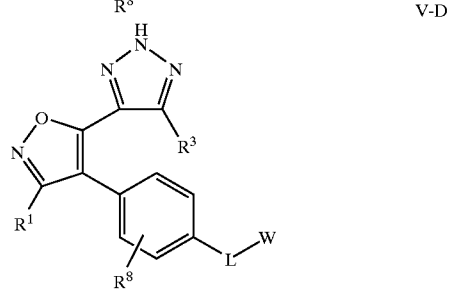

-continued

V-E

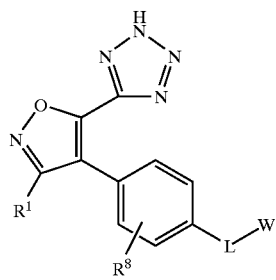

Preferred compounds of formulae V-A, V-B, V-C, V-D, and tetrazol-5-yl V-E include those having one or more, and most preferably all, of the following features: (a) Q is —CO—, —CO$_2$—, or —CONH—; (b) R$^1$ is hydrogen or NHR; (c) W is selected from R$^9$, CH(R$^9$)$_2$, CH(R$^9$)N(R$^9$)$_2$, or N(R$^9$)$_2$; (d) R$^3$ is hydrogen; (e) R$^8$, if present, is halogen, —R', —OR', —SR', —NO$_2$, —CN, or —N(R$^5$)$_2$; (f) R$^4$ is selected from —R$^6$, —NH$_2$, —NHR$^6$, —N(R$^6$)$_2$, or —NR$^6$(CH$_2$)$_y$N(R$^6$)$_2$; (g) R$^6$ is R$^5$, —(CH$_2$)$_y$CH(R$^7$)$_2$, or —(CH$_2$)$_y$R$^7$; and/or (h) R$^7$ is an optionally substituted group selected from aryl, aralkyl, heteroaryl, heteroarylalkyl, heterocyclyl, heterocyclylalkyl group.

Preferred R$^8$ substituents of the R$^2$ phenyl group include halo, nitro, haloalkyl, hydroxyalkyl, C$_{1-6}$ aliphatic, alkoxy, amino, and heterocyclyl.

Preferred L groups include —CH$_2$—, —CH$_2$NH—, —CH$_2$NHC(O)—, —NH—, —CH$_2$CH$_2$NH—, —CH$_2$O—, —CH$_2$C(O)NH—, —CH$_2$NHCH$_2$CH$_2$NHC(O)—, and —CH$_2$NHC(O)CH$_2$CH$_2$NHC(O)—.

Preferred W groups include —CH(C$_{1-6}$ aliphatic)NC(O)(C$_{1-6}$ aliphatic), —CH(CH$_2$OH)NC(O)(C$_{1-6}$ aliphatic), —CH(CH$_2$SH)NC(O)(C$_{1-6}$ aliphatic), N(C$_{1-6}$ aliphatic)$_2$, heterocyclyl (e.g. pyrrolidinyl, morpholinyl, thiomorpholinyl, and piperidinyl), —CH(C$_{1-6}$ aliphatic)NH$_2$, —CH(C$_{1-6}$ aliphatic)NC(O)O(C$_{1-6}$ aliphatic), —CH$_2$CN, and —CH$_2$N(C$_{1-6}$ aliphatic)$_2$.

When R is R$^6$, preferred R$^6$ groups include pyrrolidin-1-yl, morpholin-4-yl, piperidin-1-yl, and piperazin-1-yl wherein each group is optionally substituted. When R$^4$ is —NHR$^6$ or —N(R$^6$)$_2$, preferred R$^6$ groups further include (CH$_2$)$_y$R$^7$ and —(CH$_2$)$_y$CH(R$^7$)$_2$. Examples of preferred R$^6$ and R$^7$ include pyridin-3-yl, pyridin-4-yl, imidazolyl, furan-2-yl, tetrahydrofuran-2-yl, cyclohexyl, phenyl, -CH$_2$OH, -(CH$_2$)$_2$OH, and isopropyl, wherein each group is optionally substituted.

Exemplary structures of formula V-A, wherein R$^3$ is hydrogen and T is a valence bond, are set forth in Table 4 below.

TABLE 4

Compounds of Formula V-A

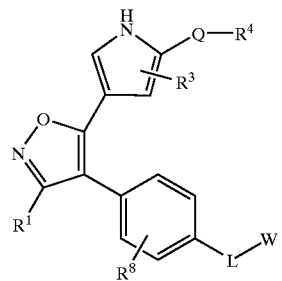

V-A

| No. | R$^1$ | R$^2$ | Q—R$^4$ |
|---|---|---|---|
| VA-1 | H | ![phenyl with CF3 and CH2NH2] | CON(Me)$_2$ |
| VA-2 | H | ![phenyl with CH2-morpholine] | CO$_2$Et |
| VA-3 | H | ![phenyl with C(O)N(CH3)2] | CONHNH$_2$ |

TABLE 4-continued
Compounds of Formula V-A
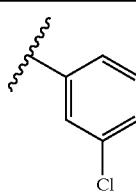
V-A
| No. | R¹ | R² | Q—R⁴ |
|---|---|---|---|
| VA-4 | NHMe | 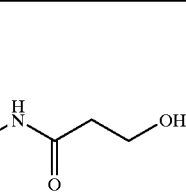 | 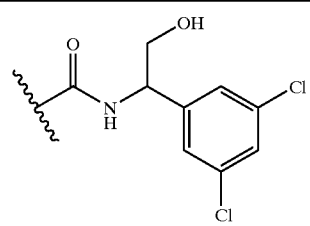 |
| VA-5 | NHMe | 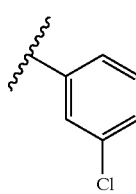 | 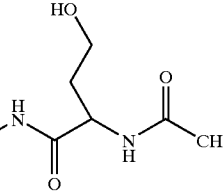 |
| VA-6 | NHMe | 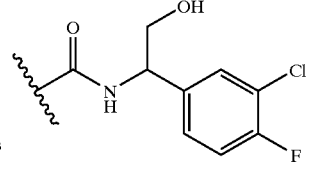 | 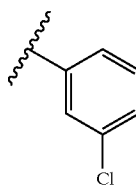 |
| VA-7 | NHEt | 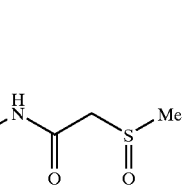 | CONHCH₂(tetrahydrofuran-2-yl) |
| VA-8 | NHMe | 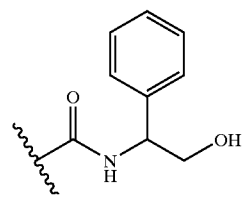 | CO(4-Me-piperidin-1-yl) |
| VA-9 | H | 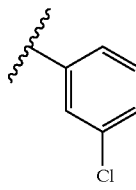 | CONHCH₂(pyrid-4-yl) |

TABLE 4-continued

Compounds of Formula V-A

| No. | R¹ | R² | Q—R⁴ |
|---|---|---|---|
| VA-10 | H | 4-(N-((S)-1-acetylpyrrolidine-2-carboxamido)methyl)-2-chlorophenyl | -C(O)NH-CH₂CH₂-(1H-imidazol-5-yl) |
| VA-11 | H | 4-((N-Boc-L-seryl-amino)methyl)-2-chlorophenyl | -C(O)NH-CH₂-(1-Boc-piperidin-3-yl) |
| VA-12 | H | 2-chloro-4-((dipropylamino)methyl)phenyl | -C(O)NH-(S)-CH(Ph)-CH₂-OC(O)CH₃ |
| VA-13 | H | 2-chloro-4-(((ethoxycarbonylmethyl)amino)methyl)phenyl | -C(O)-(4-(pyrazin-2-yl)piperazin-1-yl) |
| VA-14 | H | 2-chloro-4-(((cyanomethyl)amino)methyl)phenyl | -C(O)N(CH₂Ph)(CH₂CH₂CH₂OH) |

TABLE 4-continued
Compounds of Formula V-A
V-A
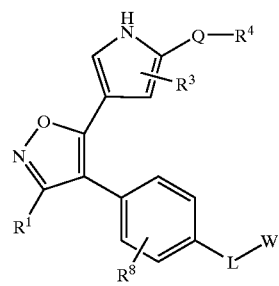
| No. | R¹ | R² | Q—R⁴ |
|---|---|---|---|
| VA-15 | NH₂ | | CONHPh |
| VA-16 | NH₂ | | CONHCH₂(pyrid-4-yl) |
| VA-17 | NH₂ | | |
| VA-18 | NH₂ | | |
| VA-19 | H | | |

TABLE 4-continued
Compounds of Formula V-A
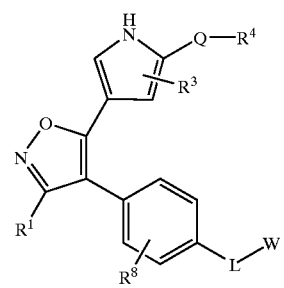
V-A
| No. | R¹ | R² | Q—R⁴ |
|---|---|---|---|
| VA-20 | H | | |
| VA-21 | H | | |
| VA-22 | Me | | |
| VA-23 | H | | |
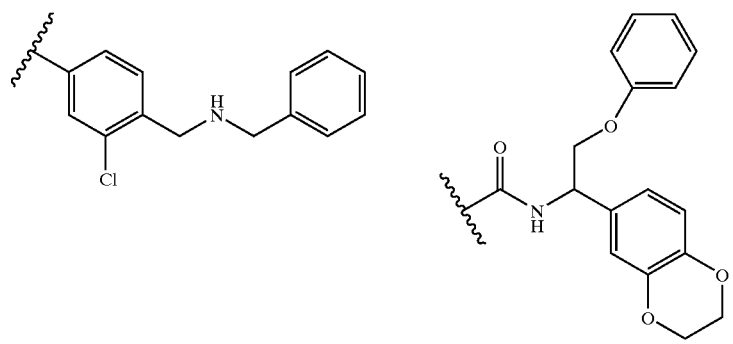
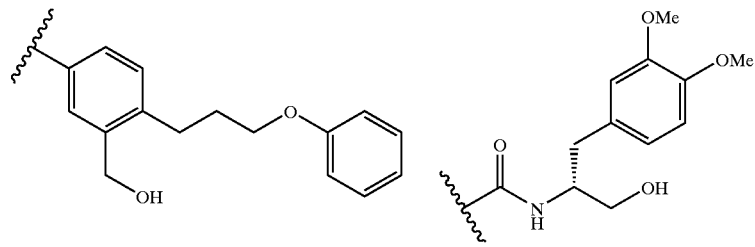
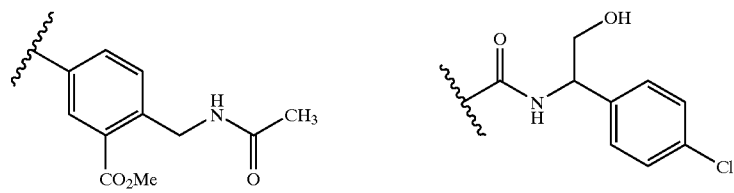
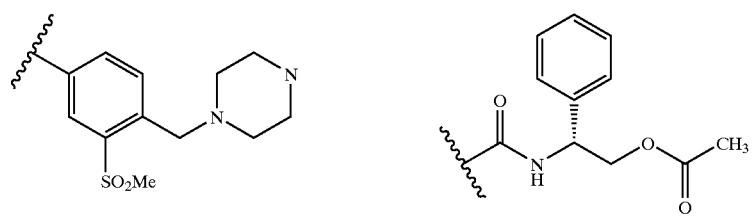

The present compounds may be prepared in general by methods known to those skilled in the art for analogous compounds, as illustrated by the general Schemes I, II, III, and IV below. These schemes are illustrated for the pyrrole compounds of this invention and, by analogy, are applicable for the preparation of compounds having the other Ht rings.

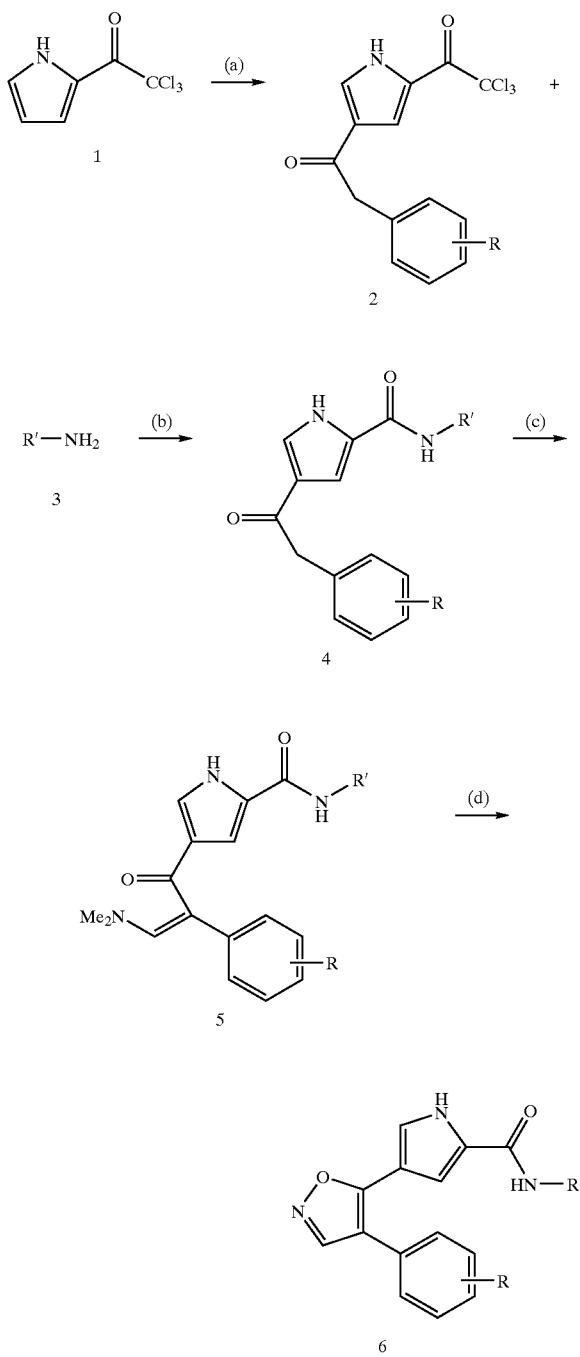

Reagents and conditions: (a) PhCH$_2$COCl, AlCl$_3$, CH$_2$Cl$_2$, 15 minutes, room temperature (b) DMF, 24 hrs, room temperature (c) (Me$_2$N)$_2$CH—Ot—Bu, THF, 48 hrs, room temperature (d) H$_2$N—OH·HCl, K$_2$CO$_3$, EtOH, 12 hrs, reflux An array of compounds of formula II-A are prepared in the following manner, as shown in Scheme I above. In step (a), a series of separate Friedel-Crafts intermediates 2 are prepared from 2-trichloroacetyl pyrrole (1) by treating a concentrated solution of the pyrrole and the appropriate acyl chloride with AlCl$_3$ in dichloroethane at 25° C. After 1 hour, the resulting slurry is purified by chromatography to afford compounds of formula 2.

In step (b), each compound 2 is first dissolved in DMF. A separate solution of 1.2 equivalents of each of six amines 3 in DMF is also prepared. Using a Bohden parallel synthesizer, each compound 2 is treated with each amine 3. The reactions are performed at ambient temperature for 24 hours then concentrated in vacuo to afford compounds of formula 4.

In step (c), the concentrates of compound 4 are dissolved in THF. Using the Bohden parallel synthesizer, each compound 4 is then treated with a solution of (Me$_2$N)$_2$CHO-t-Bu in THF. The resulting mixtures are again stirred at ambient temperature for 48 hours then concentrated in vacuo to afford compounds of formula 5.

In step (d), the concentrates of compound 5 are first dissolved in ethanol. Using the Bohden parallel synthesizer, each compound 5 is treated with K$_2$CO$_3$ and H$_2$NOH·HCl. The resulting mixtures are stirred under reflux for 12 hours then concentrated in vacuo to afford compounds of formula 6.

Each compound is purified by preparatory HPLC (Gilson) on a C18 reverse-phase column eluted with a gradient of 10–90% MeCN (0.1% TFA) in water over 15 minutes. The details of the conditions used to prepare the compounds as described in Scheme I are set forth in the Examples.

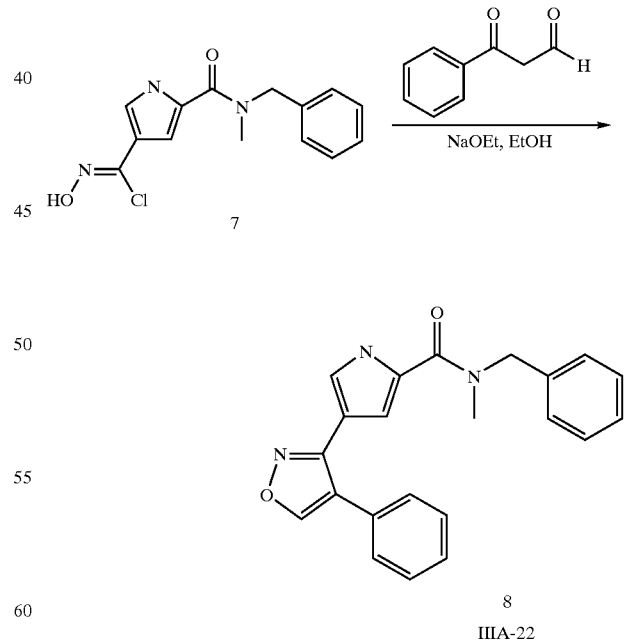

IIIA-22

As shown in Scheme II above using the preparation of compound IIIA-22 as an example, compounds of formula III-A may be prepared according to the methods of Zohdi, et al, *J. Chem. Res.*, Synop (1991) 11, pp 322–323.

Scheme III

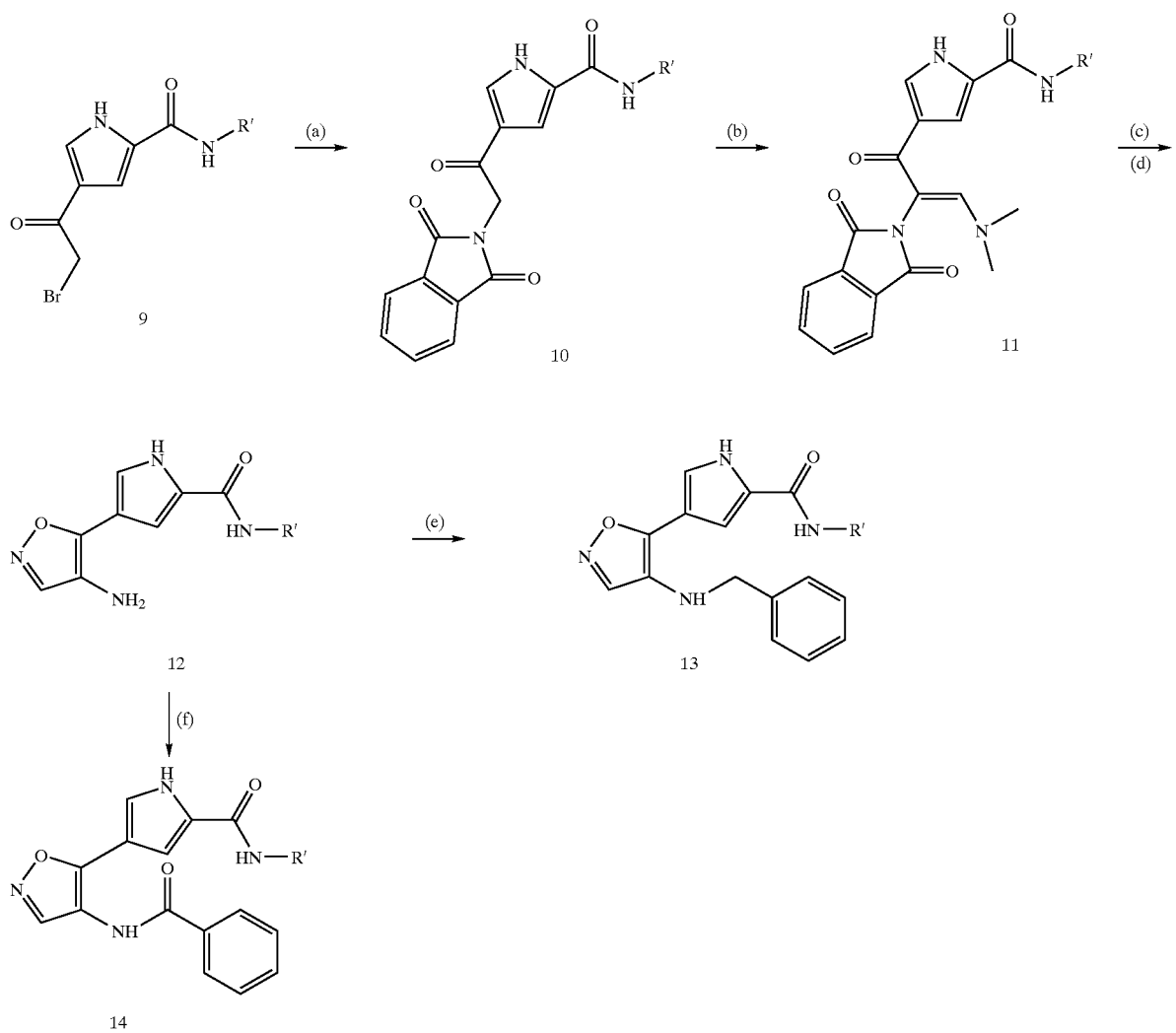

Reagents and conditions: (a) potassium phthalimide (b) Brederick's reagent (c) hydrazine (d) H$_2$N—OH•HCl, K$_2$CO$_3$, EtOH, 12 hrs, reflux (e) benzyl bromide (f) benzoyl chloride Scheme III above depicts a general method for preparing compounds of formula I wherein T is NH$_2$, NH$_2$CH$_2$, or NH$_2$C(O). In step (a), the bromoacetyl compound 9 is treated with potassium phthalimide to form the protected amino compound 10. Compound 10 is then treated with Brederick's reagent to form the enaminone compound 11. In step (c), the enaminone 11 is condensed with hydroxylamine to form the isoxazole compouns which is treated with hydrazine in step (d) to remove the phthalimide protecting group to afford the amino compound 12. The amino compound 12 may be derivatised with a variety of reagents to afford various compounds of formula I wherein T is other than a valence bond. For example, compound 12 is treated with a benzyl bromide derivative in step (e) to afford the benzylamine compound 13. In step (f), the amino compound 12 is treated with a benzoyl chloride derivative to afford the benzamide compound 14. Other compounds of formula I wherein T is other than a valence bond may be prepared by methods substantially similar to those shown in Scheme III above by modifications of which are well known to those skilled in the art.

Scheme IV

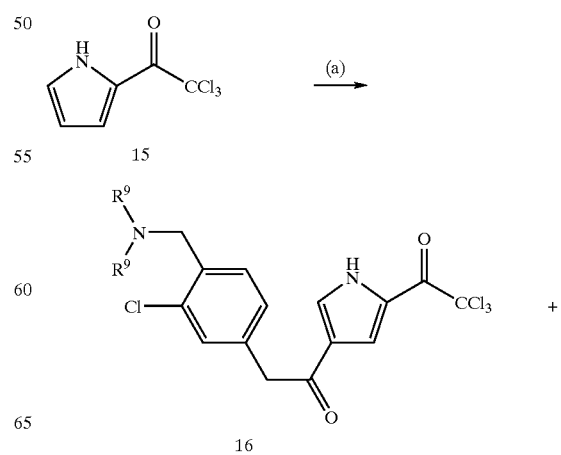

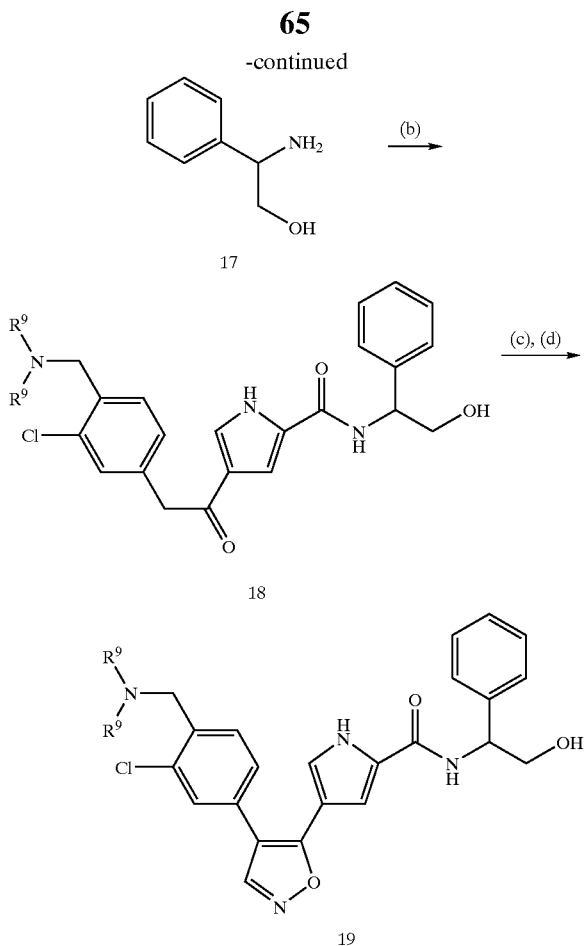

Reagents and conditions: (a) 3-Cl-4-(R$^9$)$_2$ aminomethyl-PhCH$_2$COCl, AlCl$_3$, CH$_2$Cl$_2$, 2 hours, RT (b) DMF, 24 hrs, room temperature (c) (Me$_2$N)$_2$——Ot——Bu, THF, 24 hrs, room temperature (d) H$_2$N——OH•HCl, K$_2$CO$_3$, EtOH, 12 hrs, reflux Scheme IV above shows a general synthetic route that may be used for preparing compounds of formula V-A. These compounds may be prepared by methods substantially similar to those described in Scheme I above.

According to another embodiment, the invention provides a method of inhibiting ERK or AKT kinase activity in a biological sample. This method comprises the step of contacting said biological sample with a compound of formula I:

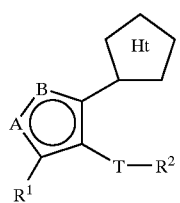

I or a pharmaceutically acceptable derivative or prodrug thereof, wherein:

Ht is a heteroaryl ring selected from pyrrol-3-yl, pyrazol-3-yl, [1,2,4]triazol-3-yl, [1,2,3]triazol-4-yl, or tetrazol-5-yl; said pyrrol-3-yl and pyrazol-3-yl each having R$^3$ and QR$^4$ substituents, and said triazole substituted by either R$^3$ or QR$^4$;

A—B is N—O or O—N;

R$^1$ is selected from R$^5$, fluorine, N(R$^5$)$_2$, OR, NRCOR, CON(R$^5$)$_2$, SO$_2$R, NRSO$_2$R, or SO$_2$N(R$^5$)$_2$;

T and Q are each independently selected from a valence bond or a linker group;

each R is independently selected from hydrogen or an optionally substituted aliphatic group having one to six carbons;

R$^2$ is selected from hydrogen, CN, fluorine, or an optionally substituted group selected from aryl, heteroaryl, heterocyclyl, an acyclic aliphatic group having one to six carbons, or a cyclic aliphatic group having four to ten carbons; wherein R$^2$ has up to one L-W substituent and up to three R$^8$ substituents;

L is a C$_{1-6}$ alkylidene chain which is optionally substituted, and wherein up to two methylene units of L are optionally replaced by —C(O)—, —C(O)C(O)—, —CONH—, —CONHNH—, —CO$_2$—, —OC(O)—, —NHCO$_2$—, —O—, —NHCONH—, —OC(O)NH—, —NHNH—, —NHCO—, —S—, —SO—, —SO$_2$—, —NH—, —SO$_2$NH—, —NHSO$_2$NH—, or —NHSO$_2$—;

W is selected from R$^9$, CH(R$^9$)$_2$, CH(R$^9$)N(R$^9$)$_2$, or N(R$^9$)$_2$;

R$^3$ is selected from R, OH, OR, N(R)$_2$, fluorine, or CN;

R$^4$ is selected from —R$^6$, —NH$_2$, —NHR$^6$, —N(R$^6$)$_2$, or —NR6 (CH$_2$)$_y$N(R$^6$)$_2$;

each R$^5$ is independently selected from hydrogen or an optionally substituted aliphatic group having one to six carbons or two R$^5$ on the same nitrogen may be taken together with the nitrogen to form a four to eight membered ring having one to three heteroatoms;

each R$^6$ is independently selected from R$^5$, —(CH$_2$)$_y$CH(R$^7$)$_2$, or —(CH$_2$)$_y$R$^7$;

y is 0–6;

each R$^7$ is an optionally substituted group independently selected from R, aryl, aralkyl, aralkoxy, heteroaryl, heteroarylalkyl, heteroarylalkoxy, heterocyclyl, heterocyclylalkyl, heterocyclylalkoxy, hydroxyalkyl, alkoxyalkyl, aryloxyalkyl, or alkoxycarbonyl; each R$^8$ is independently selected from halogen, —R', —OR', —SR', —NO$_2$, —CN, —N(R$^5$)$_2$, —NRC(O)R', —NRC(O)N(R$^5$)$_2$, —NRCO$_2$R', —NRNRC(O)R', —NRNRC(O)N(R$^5$)$_2$, —NRNRCO$_2$R', —C(O)C(O)R', —C(O)CH$_2$C(O)R', —CO$_2$R', —C(O)R', —C(O)N(R$^5$)$_2$, —OC(O)N(R$^5$)$_2$, —S(O)$_2$R', —SO$_2$N(R$^5$)$_2$, —S(O)R', —NRSO$_2$N(R$^5$)$_2$, —NRSO$_2$R', —C(=S)N(R$^5$)$_2$, or —C(=NH)N(R$^5$)$_2$;

wherein each R' is independently selected from hydrogen, or an optionally substituted group selected from aliphatic, heteroaryl, heterocyclyl, or phenyl; and each R$^9$ is independently selected from R$_5$, R$^8$, or an optionally substituted group selected from aryl, aralkyl, aralkoxy, heteroaryl, heteroaralkyl, heterocyclyl, or heterocyclylalkyl.

According to a preferred embodiment, the invention relates to a method of inhibiting ERK or AKT kinase activity in a biological sample comprising the step of contacting said biological sample with a compound of formula II, III, IV, or V; more preferably with a compound of formula II-A, III-A, IV-A, or V-A; and most preferably, with a compound listed in Tables 1–4.

The term "biological sample", as used herein includes cell cultures or extracts thereof; biopsied material obtained from a mammal or extracts thereof; and blood, saliva, urine, feces, semen, tears, or other body fluids or extracts thereof.

Another aspect of this invention relates to a method for treating a disease in a patient that is alleviated by treatment with an ERK or AKT protein kinase inhibitor, which method comprises administering to a patient in need thereof a therapeutically effective amount of a compound of formula I:

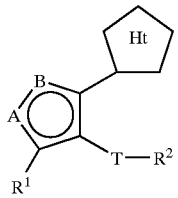

or a pharmaceutically acceptable derivative or prodrug thereof, wherein:

Ht is a heteroaryl ring selected from pyrrol-3-yl, pyrazol-3-yl, [1,2,4]triazol-3-yl, [1,2,3]triazol-4-yl, or tetrazol-5-yl; said pyrrol-3-yl and pyrazol-3-yl each having $R^3$ and $QR^4$ substituents, and said triazole substituted by either $R^3$ or $QR^4$;

A—B is N—O or O—N;

$R^1$ is selected from $R^5$, fluorine, $N(R^5)_2$, OR, NRCOR, CON$(R^5)_2$, $SO_2R$, $NRSO_2R$, or $SO_2N(R^5)_2$;

T and Q are each independently selected from a valence bond or a linker group;

each R is independently selected from hydrogen or an optionally substituted aliphatic group having one to six carbons;

$R^2$ is selected from hydrogen, CN, fluorine, or an optionally substituted group selected from aryl, heteroaryl, heterocyclyl, an acyclic aliphatic group having one to six carbons, or a cyclic aliphatic group having four to ten carbons; wherein $R^2$ has up to one L-W substituent and up to three $R^8$ substituents;

L is a $C_{1-6}$ alkylidene chain which is optionally substituted, and wherein up to two methylene units of L are optionally replaced by —C(O)—, —C(O)C(O)—, —CONH—, —CONHNH —, —CO$_2$, —OC(O)—, —NHCO$_2$—, —O—, —NHCONH—, —OC(O)NH—, —NHNH—, —NHCO—, —S—, —SO—, —SO$_2$—, —NH—, —SO$_2$NH—, —NHSO$_2$NH—, or —NHSO$_2$—;

W is selected from $R^9$, CH$(R^9)_2$, CH$(R^9)N(R^9)_2$, or $N(R^9)_2$;

$R^3$ is selected from R, OH, OR, N(R)$_2$, fluorine, or CN;

$R^4$ is selected from —$R^6$, —NH$_2$, —NHR$^6$, —N(R$^6$)$_2$, or —NR$^6$ (CH$_2$)$_y$N(R$^6$)$_2$;

each $R^5$ is independently selected from hydrogen or an optionally substituted aliphatic group having one to six carbons or two $R^5$ on the same nitrogen may be taken together with the nitrogen to form a four to eight membered ring having one to three heteroatoms;

each $R^6$ is independently selected from $R^5$, —(CH$_2$)$_y$CH(R$^7$)$_2$, or —(CH$_2$)$_y$R$^7$;

y is 0–6;

each $R^7$ is an optionally substituted group independently selected from R, aryl, aralkyl, aralkoxy, heteroaryl, heteroarylalkyl, heteroarylalkoxy, heterocyclyl, heterocyclylalkyl, heterocyclylalkoxy, hydroxyalkyl, alkoxyalkyl, aryloxyalkyl, or alkoxycarbonyl;

each $R^8$ is independently selected from halogen, —R', —OR', —SR', —NO$_2$, —CN, —N(R$^5$)$_2$, —NRC(O)R', —NRC(O)N(R$^5$)$_2$, —NRCO$_2$R', —NRNRC(O)R', —NRNRC(O)N(R$^5$)$_2$, —NRNRCO$_2$R', —C(O)C(O)R', —C(O)CH$_2$C(O)R', —CO$_2$R', —C(O)R', —C(O)N(R$^5$)$_2$, —OC(O)N(R$^5$)$_2$, —S(O)$_2$R', —SO$_2$N(R$^5$)$_2$, —S(O)R', —NRSO$_2$N(R$^5$)$_2$, —NRSO$_2$R', —C(=S)N(R$^5$)$_2$, or —C(=NH)N(R$^5$)$_2$;

wherein each R' is independently selected from hydrogen, or an optionally substituted group selected from aliphatic, heteroaryl, heterocyclyl, or phenyl; and each $R^9$ is independently selected from $R^5$, $R^8$, or an optionally substituted group selected from aryl, aralkyl, aralkoxy, heteroaryl, heteroaralkyl, heterocyclyl, or heterocyclylalkyl.

A preferred embodiment comprises administering a compound of formula II, III, IV, or V, more preferably a compound of formula II-A, III-A, IV-A, or V-A, and most preferably, a compound listed in Tables 1–4.

Pharmaceutical compositions useful for such methods are described below and are another aspect of the present invention.

The present method is especially useful for treating a disease that is alleviated by the use of an inhibitor of ERK.

The activity of the compounds as protein kinase inhibitors, for example as ERK inhibitors, may be assayed in vitro, in vivo or in a cell line. Using ERK as an example, in vitro assays include assays that determine inhibition of either the kinase activity or ATPase activity of activated ERK. Alternate in vitro assays quantitate the ability of the inhibitor to bind to ERK and may be measured either by radiolabelling the inhibitor prior to binding, isolating the inhibitor/ERK complex and determining the amount of radiolabel bound, or by running a competition experiment where new inhibitors are incubated with ERK bound to known radioligands. One may use any type or isoform of ERK, depending upon which ERK type or isoform is to be inhibited.

The protein kinase inhibitors of this invention, or pharmaceutical salts thereof, may be formulated into pharmaceutical compositions for administration to animals or humans. These pharmaceutical compositions effective to treat or prevent a protein kinase-mediated condition which comprise the protein kinase inhibitor in an amount sufficient to measurably inhibit protein kinase activity (e.g., ERK or AKT activity) and a pharmaceutically acceptable carrier, are another embodiment of the present invention. The term "measurably inhibit", as used herein means a measurable change in activity between a sample containing said inhibitor and a sample containing only protein kinase.

The compounds of this invention are inhibitors of ERK and AKT kinase as determined by enzymatic assay. The details of the conditions used for the enzymatic assays are set forth in the Examples hereinbelow. Accordingly, these compounds are useful for treating ERK- or AKT-mediated diseases or conditions.

The term "ERK-mediated disease" or "condition", as used herein means any disease or other deleterious condition in which ERK is known to play a role. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

The term "AKT-mediated disease" or "condition", as used herein, means any disease or other deleterious condition in which AKT is known to play a role. AKT-mediated diseases or conditions include, but are not limited to, proliferative disorders, cancer, and neurodegenerative disorders.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound. of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes. of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of ERK or AKT inhibitor that may be combined with the carrier materials to produce a single dosage form will vary depending upon the host treated, the particular mode of administration. Preferably, the compositions should be formulated so that a dosage of between about 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

The kinase inhibitors of this invention or pharmaceutical compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Implantable devices coated with a kinase inhibitor of this invention are another embodiment of the present invention.

According to another embodiment, the invention provides methods for treating or preventing an ERK- or AKT-mediated condition comprising the step of administering to a patient one of the above-described pharmaceutical compositions. The term "patient", as used herein, means an animal, preferably a mammal, and most preferably a human.

Preferably, that method is used to treat or prevent a condition selected from cancers such as cancers of the breast, colon, prostate, skin, pancreas, brain, genitourinary tract, lymphatic system, stomach, larynx and lung, including lung adenocarcinoma and small cell lung cancer, stroke, diabetes, hepatomegaly, cardiomegaly, Alzheimer's disease, cystic fibrosis, and viral disease, or any specific disease or disorder described above.

Depending upon the particular ERK- or AKT-mediated condition to be treated or prevented, additional therapeutic agents, which are normally administered to treat or prevent that condition, may be administered together with the ERK or AKT inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of therapeutic agents the inhibitors of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues., alpha glucosidase inhibitors, biguanides, and insulin sensitizers; and agents for treating immunodeficiency disorders such as gamma globulin.

These additional therapeutic agents may be administered separately, as part of a multiple dosage regimen, from the kinase inhibitor-containing composition. Alternatively, these agents may be part of a single dosage form, mixed together with the inhibitor in a single composition.

In order that the invention described herein may be more fully understood, the following examples are set forth. It should be understood that these examples are for illustrative purposes only and are not to be construed as limiting this invention in any manner.

EXAMPLES

Example 1

Compounds of formula II-A were prepared in the following manner in parallel fashion, as shown in Scheme I depicted above. In step (a), a series of separate Friedel-Crafts intermediates 2 were prepared from 2-trichloroacetyl pyrrole (1) by treating a concentrated solution of the pyrrole (1 equivalent) and the appropriate acyl chloride (1 equivalent) with $AlCl_3$ (1 equivalent) in minimal dichloroethane at 25° C. After 1 hour, the resulting slurry was purified by silica gel chromatography to afford compounds of formula 2.

In step (b), each compound 2 was first dissolved in DMF. A separate solution of 1.2 equivalents of each of six amines 3 in DMF was also prepared. Using a Bohden parallel synthesizer, each compound 2 was treated with each amine 3. The reactions were performed at ambient temperature for 24 hours then concentrated in vacuo to afford compounds of formula 4.

In step (c), the concentrates of compound 4 were dissolved in THF. Using the Bohden parallel synthesizer, each compound 4 was then treated with a solution of $(Me_2N)_2CH$—O-t-Bu (10 equivalents) in THF. The resulting mixtures were again stirred at ambient temperature for 48 hours then concentrated in vacuo to afford compounds of formula 5.

In step (d), the concentrates of compound 5 were first dissolved in ethanol. Using the Bohden parallel synthesizer, each compound 5 was treated with $K_2CO_3$ (2 equivalents) and $H_2NOH\cdot HCl$ (2.0 equivalents). The resulting mixtures were stirred at reflux for 12 hours then concentrated in vacuo to afford compounds of formula 6.

Each compound was purified by preparatory HPLC (Gilson) on a C18 reverse-phase column eluted with a gradient of 10–90% MeCN (0.1% TFA) in water over 15 minutes. The characterization data for these compounds is summarized in Table 5 below and includes LC/MS, HPLC, and $^1$H NMR data.

Unless otherwise indicated, the HPLC method used for the determination of retention time is as follows: on a YMC ODS-AQ 55 120A column with a size of 3.0×150 mm, a gradient of water:MeCN, 0.1% TFA (95:5→0:100) was run over 15 minutes at 1 mL/min and 214 nm.

As used herein, the term "$R_t$" refers to the retention time, in minutes, obtained for the compound using the HPLC method as indicated.

Where applicable, $^1$H NMR data is also summarized in Table 5 below wherein "Y" designates $^1$H NMR data is available and was found to be consistant with structure. Compound numbers correspond to the compound numbers listed in Table 1.

TABLE 5

Characterization Data for Selected Compounds

| Compound No IIA- | M + 1 | M − 1 | HPLC Purity (%) | $R_t$ (min) | $^1$H NMR |
|---|---|---|---|---|---|
| 1 | 282 | — | 100 | 8.6 | Y |
| 3 | 358 | 356 | 75 | 9.61 | — |
| 6 | 363 | 361 | 100 | — | — |
| 15 | 381 | 379 | 93 | — | — |
| 16 | 381 | 379 | 100 | — | — |
| 17 | 381 | 379 | 100 | — | — |
| 23 | 374 | 372 | 100 | — | — |
| 24 | 374 | 372 | 100 | — | — |
| 29 | 425 | 423 | 98 | — | — |
| 30 | 401 | 399 | 100 | — | — |
| 31 | 401 | 399 | 98 | — | — |
| 32 | 401 | 399 | 100 | — | — |
| 36 | 354 | 352 | 96 | — | — |
| 37 | 384 | — | 90 | — | — |
| 38 | 360 | 358 | 100 | — | — |
| 39 | 360 | 358 | 75 | — | — |
| 42 | 355 | 354 | 100 | — | — |
| 43 | 365 | 363 | 100 | — | — |
| 44 | 397 | — | 92 | — | — |
| 45 | 373 | 371 | 100 | — | — |
| 46 | 373 | 371 | 100 | — | — |
| 47 | 354 | 352 | 85 | 7.92 | Y |
| 48 | 379 | 377 | 84 | 7.96 | — |
| 49 | 372 | 370 | 90 | 9.82 | — |
| 50 | 399 | 397 | 87 | 8.37 | — |
| 51 | 371 | 369 | 83 | 7.56 | — |
| 52 | 379 | 377 | 100 | 8.02 | — |
| 53 | 379 | 377 | 100 | 7.83 | — |
| 54 | 372 | 370 | 95 | 9.91 | — |
| 55 | 399 | 397 | 95 | 8.44 | — |
| 56 | 358 | 356 | 73 | 9.64 | — |
| 57 | 371 | 369 | 83 | 7.66 | — |
| 58 | 413 | 411 | 93 | 8.6 | — |
| 59 | 433 | 431 | 100 | 9.09 | — |
| 60 | 392 | 390 | 74 | 10.35 | — |
| 61 | 405 | 403 | 70 | 8.26 | — |
| 62 | 397 | 395 | 100 | 7.99 | — |
| 63 | 397 | 395 | 100 | 7098 | — |
| 64 | 390 | 388 | 100 | 9.75 | — |
| 65 | 417 | 415 | 89 | 8.42 | — |
| 66 | — | — | 86 | 9.54 | — |
| 67 | 389 | 387 | 68 | 7.67 | — |
| 68 | — | — | 89 | 8.1 | — |
| 69 | — | — | 100 | 8.13 | — |
| 70 | 390 | — | 81 | 10.01 | — |
| 71 | 417 | 415 | 100 | 8.56 | — |
| 72 | 376 | 374 | 96 | 9.75 | — |
| 73 | 389 | 387 | 62 | 7.78 | — |
| 74 | 405 | 403 | 97 | 6.9 | — |
| 75 | 405 | 403 | 93 | 6.9 | — |
| 76 | 398 | 396 | 85 | 8.43 | — |
| 77 | 425 | 423 | 100 | 7.27 | — |
| 78 | 384 | 382 | 83 | 8.1 | — |
| 79 | 397 | 395 | 98 | 6.59 | — |
| 80 | 389 | 387 | 100 | 7.29 | — |
| 81 | 389 | 387 | 100 | 7.29 | — |
| 82 | 382 | 380 | 100 | 8.91 | — |
| 83 | 409 | 407 | 100 | 7.7 | — |
| 84 | 368 | — | 88 | 8.65 | — |
| 85 | 381 | 379 | 80 | 6.97 | — |
| 86 | 413 | 411 | 100 | 8.69 | — |
| 87 | 413 | 411 | 100 | 8.67 | — |
| 88 | 406 | 404 | 72 | 10.84 | — |
| 89 | 433 | 431 | 100 | 9.13 | — |
| 90 | 392 | 390 | 72 | 10.54 | — |
| 91 | 405 | 403 | 74 | 8.26 | — |
| 92 | — | — | 92 | — | Y |
| 93 | 358 | 356 | 100 | — | Y |

Example 2

ERK Inhibition Assay:

Compounds were assayed for the inhibition of ERK2 by a spectrophotometric coupled-enzyme assay (Fox et al (1998) *Protein Sci* 7, 2249). In this assay, a fixed concentration of activated ERK2 (10 nM) was incubated with various concentrations of the compound in DMSO (2.5%) for 10 min. at 30° C. in 0.1 M HEPES buffer, pH 7.5, containing 10 mM MgCl$_2$, 2.5 mM phosphoenolpyruvate, 200 μM NADH, 150 μg/mL pyruvate kinase, 50 μg/mL lactate dehydrogenase, and 200 μM erktide peptide. The reaction was initiated by the addition of 65 μM ATP and the rate of decrease of absorbance at 340 nM was monitored. The percent inhibition values were determined at an inhibitor concentration of 10 μM.

Table 6 shows the results of the activity of selected compounds of this invention in the ERK2 inhibition assay. The compound numbers correspond to the compound numbers in Table 1. Compounds having an activity designated as "A" provided a percent inhibition value above 60%; compounds having an activity designated as "B" provided a percent inhibition value between 30 and 60%; and compounds having an activity designated as "C" provided a percent inhibition value less than 30%.

TABLE 6

ERK2 Inhibitory Activity of Selected Compounds

| No. | Activity |
|---|---|
| IIA-1 | B |
| IIA-3 | B |
| IIA-4 | C |
| IIA-5 | B |
| IIA-6 | C |
| IIA-7 | C |
| IIA-8 | A |
| IIA-9 | A |
| IIA-10 | A |
| IIA-11 | B |
| IIA-12 | B |
| IIA-13 | B |
| IIA-15 | B |
| IIA-16 | B |
| IIA-17 | B |
| IIA-18 | C |
| IIA-19 | B |
| IIA-20 | B |
| IIA-22 | C |
| IIA-23 | B |
| IIA-24 | A |
| IIA-25 | C |
| IIA-26 | C |
| IIA-27 | C |
| IIA-28 | C |
| IIA-29 | C |
| IIA-36 | B |
| IIA-37 | C |
| IIA-38 | B |
| IIA-39 | B |
| IIA-40 | C |
| IIA-41 | C |
| IIA-42 | C |
| IIA-43 | C |
| IIA-44 | C |
| IIA-45 | C |
| IIA-46 | C |
| IIA-47 | A |
| IIA-48 | A |
| IIA-49 | B |
| IIA-50 | C |
| IIA-51 | C |
| IIA-52 | A |
| IIA-53 | B |
| IIA-54 | C |
| IIA-55 | C |
| IIA-56 | C |
| IIA-57 | C |
| IIA-58 | B |
| IIA-59 | C |
| IIA-60 | B |
| IIA-61 | C |

TABLE 6-continued

ERK2 Inhibitory Activity of Selected Compounds

| No. | Activity |
|---|---|
| IIA-62 | A |
| IIA-63 | A |
| IIA-64 | B |
| IIA-65 | C |
| IIA-66 | B |
| IIA-67 | C |
| IIA-68 | A |
| IIA-69 | B |
| IIA-70 | B |
| IIA-71 | C |
| IIA-72 | B |
| IIA-73 | C |
| IIA-74 | B |
| IIA-80 | B |
| IIA-81 | B |
| IIA-82 | B |
| IIA-84 | C |
| IIA-86 | A |
| IIA-87 | B |
| IIA-88 | B |
| IIA-90 | C |
| IIA-91 | C |
| IIA-106 | B |
| IIA-107 | B |
| IIA-108 | B |
| IIA-109 | B |
| IIA-110 | B |
| IIA-111 | B |
| IIA-112 | A |
| IIA-113 | B |
| IIA-114 | A |
| IIA-115 | B |
| IIA-116 | B |
| IIA-117 | C |
| IIA-118 | C |
| IIA-119 | B |
| IIA-120 | A |
| IIA-121 | B |
| IIA-122 | C |
| IIA-123 | C |
| IIA-124 | C |
| IIA-125 | C |
| IIA-126 | B |
| IIA-127 | B |
| IIA-130 | B |
| IIA-131 | C |
| IIA-132 | C |
| IIA-133 | B |
| IIA-134 | A |
| IIA-135 | C |
| IIA-136 | C |
| IIA-137 | C |
| IIA-138 | C |
| IIA-139 | C |
| IIA-140 | B |
| IIA-141 | C |
| IIA-142 | C |
| IIA-143 | A |
| IIA-144 | A |
| IIA-145 | B |
| IIA-146 | B |
| IIA-147 | B |
| IIA-148 | B |
| IIA-149 | C |
| IIA-150 | B |
| IIA-151 | B |
| IIA-152 | C |

TABLE 6-continued

ERK2 Inhibitory Activity of Selected Compounds

| No. | Activity |
|---|---|
| IIA-153 | C |
| IIA-155 | B |
| IIA-156 | C |
| IIA-157 | C |
| IIA-158 | B |
| IIA-159 | C |
| IIA-160 | B |
| IIA-161 | C |
| IIA-162 | C |
| IIA-164 | C |
| IIA-165 | C |
| IIA-166 | C |
| IIA-167 | B |
| IIA-171 | A |
| IIA-172 | B |
| IIA-173 | C |
| IIA-174 | C |
| IIA-175 | A |
| IIA-176 | C |
| IIA-177 | C |
| IIA-178 | C |
| IIA-179 | C |
| IIA-180 | C |
| IIA-181 | C |
| IIA-182 | B |
| IIA-183 | B |
| IIA-184 | C |
| IIA-185 | C |
| IIA-186 | C |
| IIA-187 | C |
| IIA-188 | C |
| IIA-189 | B |
| IIA-190 | C |
| IIA-191 | C |

Example 3

AKT3 Inhibition Assay:

Compounds were screened for their ability to inhibit AKT3 using a standard coupled enzyme assay (Fox et al., Protein Sci., (1998) 7, 2249). Assays were carried out in a mixture of 100 mM HEPES 7.5, 10 mM MgCl2, 25 mM NaCl , 1 mM DTT and 1.5% DMSO. Final substrate concentrations in the assay were 170 μM ATP (Sigma Chemicals) and 200 uM peptide (RPRAATF, American Peptide, Sunnyvale, Calif.). Assays were carried out at 30° C. and 45 nM AKT3. Final concentrations of the components of the coupled enzymeisystem were 2.5 mM phosphoenolpyruvate, 300 μM NADH, 30 μg/ML pyruvate kinase and 10 μg/ml lactate dehydrogenase.

An assay stock buffer solution was prepared containing all of the reagents listed above, with the exception of AKT3, DTT, and the test compound of interest. 56 μl of the stock solution was placed in a 384 well plate followed by addition of 1 μl of 2 mM DMSO stock containing the test compound (final compound concentration 30 μM). The plate was pre-incubated for about 10 minutes at 30° C. and the reaction initiated by addition of 10 μl of enzyme (final concentration 45 nM) and 1 mM DTT. Rates of reaction were obtained using a BioRad Ultramark plate reader (Hercules, Calif.) over a 5 minute read time at 30° C.

Table 7 shows the results of the activity of selected compounds of this invention in the AKT3 inhibition assay. The compound numbers correspond to the compound numbers in Table 1. Compounds having an activity designated as "A" provided a percent inhibition value above 30%; compounds having an activity designated as "B" provided a percent inhibition value between 20 and 30%; and compounds having an activity designated as "C" provided a percent inhibition value less than 20%. All percent inhibition values were determined at a 30 μM inhibitor concentration.

TABLE 7

AKT3 Inhibitory Activity of Selected Compounds

| No. | Activity |
|---|---|
| IIA-106 | B |
| IIA-107 | A |
| IIA-108 | B |
| IIA-109 | A |
| IIA-110 | B |
| IIA-111 | B |
| IIA-112 | B |
| IIA-113 | B |
| IIA-114 | A |
| IIA-115 | B |
| IIA-116 | A |
| IIA-117 | A |
| IIA-118 | A |
| IIA-119 | A |
| IIA-120 | A |
| IIA-121 | C |
| IIA-122 | A |
| IIA-123 | A |
| IIA-124 | C |
| IIA-125 | C |
| IIA-126 | B |
| IIA-127 | B |
| IIA-131 | C |
| IIA-132 | B |
| IIA-133 | C |
| IIA-134 | C |
| IIA-135 | C |
| IIA-136 | C |
| IIA-139 | C |
| IIA-140 | C |
| IIA-141 | C |
| IIA-142 | C |
| IIA-143 | A |
| IIA-144 | C |
| IIA-145 | C |
| IIA-146 | C |
| IIA-147 | C |
| IIA-148 | C |
| IIA-150 | C |
| IIA-151 | B |
| IIA-153 | A |
| IIA-155 | C |
| IIA-156 | C |
| IIA-159 | C |
| IIA-160 | C |
| IIA-161 | C |
| IIA-162 | C |
| IIA-163 | A |
| IIA-164 | A |
| IIA-165 | C |
| IIA-166 | C |
| IIA-167 | C |
| IIA-171 | C |
| IIA-172 | B |
| IIA-173 | B |
| IIA-174 | C |
| IIA-175 | C |
| IIA-176 | C |
| IIA-177 | C |
| IIA-178 | C |
| IIA-179 | C |
| IIA-180 | A |
| IIA-181 | C |
| IIA-182 | B |
| IIA-183 | C |
| IIA-184 | C |
| IIA-185 | C |
| IIA-186 | C |

TABLE 7-continued

AKT3 Inhibitory Activity of Selected Compounds

| No. | Activity |
|---|---|
| IIA-187 | C |
| IIA-188 | C |
| IIA-189 | B |
| — | — |

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:

1. A compound of formula I:

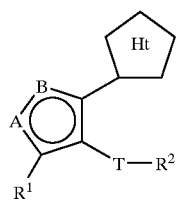

I or a pharmaceutically acceptable salt thereof, wherein:

Ht is pyrrol-3-yl; said pyrrol-3-yl having $R^3$ and $QR^4$ substituents;

A—B is N—O or O—N;

$R^1$ is hydrogen or NHR;

T is a valence bond;

Q is —C(O)— or —SO$_2$—;

each R is independently selected from hydrogen or an optionally substituted aliphatic group having one to six carbons;

$R^2$ is an aryl group substituted with up to three $R^8$ substituents;

$R^3$ is hydrogen;

$R^4$ is —NHR$^6$;

$R^6$ is —(CH$_2$)$_y$CH(R$^7$)$_2$;

y is 0–6;

each $R^7$ is independently selected from R, aryl, or hydroxyalkyl, wherein said aryl ring is optionally substituted with halogen, R', OR', CO$_2$R', or SO$_2$R', wherein each R' is independently selected from hydrogen or a C$_{1-6}$ aliphatic group; and each $R^8$ is independently selected from halogen, —R', or —OR'; wherein each R' is independently selected from hydrogen or an optionally substituted aliphatic group.

2. The compound according to claim 1 having the formula:

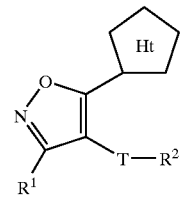

II wherein the variables Ht, T, $R^1$ and $R^2$ are as defined in claim 1, or a pharmaceutically acceptable salt thereof.

3. The compound according to claim 2 having the formula:

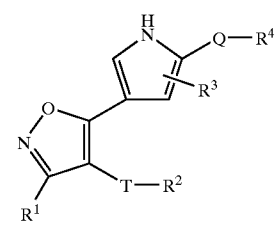

II-A wherein the variables Q, T, $R^1$, $R^2$, $R^3$, and $R^4$ are as defined in claim 1, or a pharmaceutically acceptable salt thereof.

4. The compound according to claim 1 having the formula:

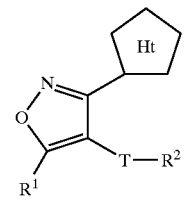

III wherein the variables Ht, T, $R^1$, and $R^2$ are as defined in claim 1, or a pharmaceutically acceptable salt thereof.

5. The compound according to claim 4 having the formula:

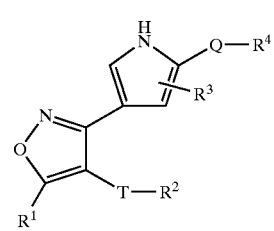

III-A wherein the variables Q, T, $R^1$, $R^2$, $R^3$, and $R^4$ are as defined in claim 1, or a pharmaceutically acceptable salt thereof.

6. The compound according to claim 1 having the formula:

IV

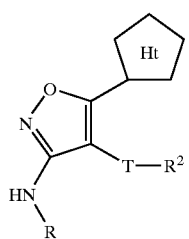

wherein the variables Ht, T, R, and $R^2$ are as defined in claim 1, or a pharmaceutically acceptable salt thereof.

7. The compound according to claim 6 having the formula:

IV-A

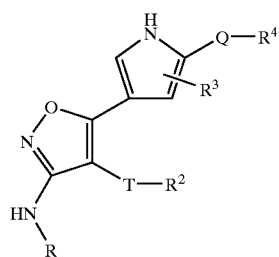

wherein the variables Q, T, R, $R^2$, $R^3$, and $R^4$ are as defined in claim 1, or a pharmaceutically acceptable salt thereof.

8. The compound according to claim 1, wherein said compound is selected from:

IIA-128

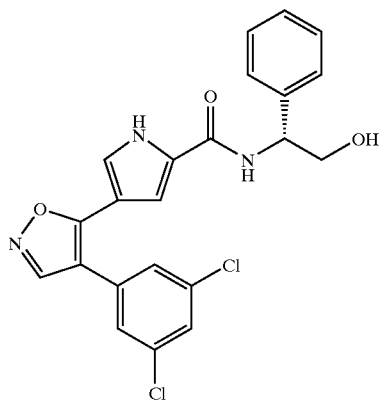

IIA-129

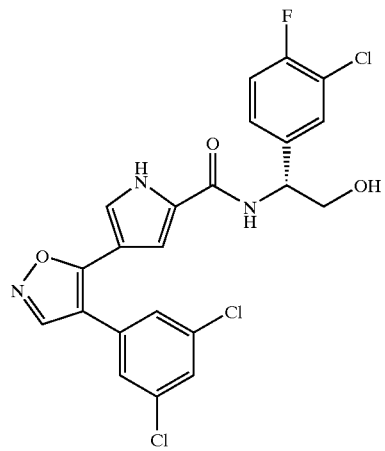

IVA-24

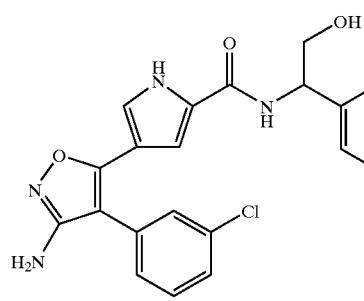

or

IVA-25

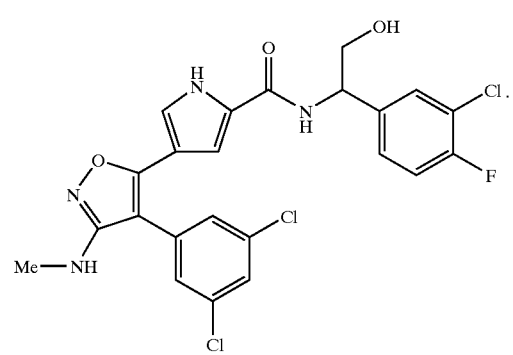

.

9. A composition comprising a compound according to any one of claims 1, 2, 3, 4, 5, 6, 7, or 8; and a pharmaceutically acceptable carrier.

10. The composition according to claim 9, wherein said compound is formulated in a pharmaceutically acceptable manner for administration to a patient.

* * * * *